United States Patent
Ito et al.

(10) Patent No.: US 8,202,213 B2
(45) Date of Patent: Jun. 19, 2012

(54) MEDICAL DEVICE

(75) Inventors: Seiichi Ito, Hachioji (JP); Shunya Akimoto, Kawasaki (JP); Junichi Onishi, Hachioji (JP); Akira Suzuki, Uenohara (JP); Soichi Ikuma, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 310 days.

(21) Appl. No.: 12/469,000

(22) Filed: May 20, 2009

(65) Prior Publication Data
US 2009/0292171 A1 Nov. 26, 2009

(30) Foreign Application Priority Data
May 23, 2008 (JP) ................ 2008-135633

(51) Int. Cl.
*A61B 1/00* (2006.01)
*A61B 1/06* (2006.01)
(52) U.S. Cl. .............. 600/117; 600/103; 600/109
(58) Field of Classification Search ............ 600/109, 600/103, 117–118, 160, 173; 128/922
See application file for complete search history.

(56) References Cited

U.S. PATENT DOCUMENTS

| | | | | |
|---|---|---|---|---|
| 5,331,947 | A * | 7/1994 | Shturman | 600/115 |
| 5,704,897 | A | 1/1998 | Truppe | |
| 5,776,050 | A * | 7/1998 | Chen et al. | 600/117 |
| 6,773,393 | B1 * | 8/2004 | Taniguchi et al. | 600/117 |
| 7,195,587 | B2 | 3/2007 | Taniguchi et al. | |
| 7,901,348 | B2 | 3/2011 | Soper et al. | |
| 7,940,967 | B2 * | 5/2011 | Ozaki et al. | 382/128 |
| 7,951,070 | B2 | 5/2011 | Ozaki et al. | |
| 2005/0033117 | A1 | 2/2005 | Ozaki et al. | |
| 2005/0085718 | A1 | 4/2005 | Shahidi | |
| 2005/0182295 | A1 * | 8/2005 | Soper et al. | 600/117 |
| 2006/0149134 | A1 | 7/2006 | Soper et al. | |
| 2007/0060792 | A1 | 3/2007 | Draxinger et al. | |
| 2007/0293721 | A1 | 12/2007 | Gilboa | |

FOREIGN PATENT DOCUMENTS
EP 1 543 765 A1 6/2005
(Continued)

OTHER PUBLICATIONS
JP 2003265408 A Machine Translated Japanese Patent.*
(Continued)

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

A medical device for examination or treatment based on a reference point, includes: a virtual endoscopic image generation section configured to generate a virtual endoscopic image of a bronchus from a plurality of different line-of-sight positions using three-dimensional image data of the bronchus of a subject that is obtained in advance; an image retrieval section configured to retrieve a virtual endoscopic image highly similar to an endoscopic image of the bronchus picked up by an image pickup section arranged at a distal end portion of an insertion section; a reference-point setting section configured to set a reference point based on a line-of-sight position of the highly similar virtual endoscopic image; and a relative-position calculation section configured to calculate a relative position of a treatment instrument to the reference point.

6 Claims, 22 Drawing Sheets

FOREIGN PATENT DOCUMENTS

| | | |
|---|---|---|
| JP | 2000-135215 | 5/2000 |
| JP | 2002-119507 | 4/2002 |
| JP | 2003265408 A * | 9/2003 |
| JP | 2004-89484 | 3/2004 |
| JP | 2004-180940 | 7/2004 |
| JP | 2005-131042 | 5/2005 |
| WO | 2007/008289 | 1/2007 |

OTHER PUBLICATIONS

Bricault et al., "Registration of Real and CT-Derived Virtual Bronchoscopic Images to Assist Transbronchial Biopsy", pp. 703-714, IEEE Transactions on Medical Imaging, vol. 17, No. 5, Oct. 1998, XP011035768.

JP 2003265408A—Machine Translation.

U.S. Office Action dated Jul. 26, 2011 in related U.S. Appl. No. 12/468,277.

U.S. Office Action dated Oct. 19, 2011 in related U.S. Appl. No. 12/469,111.

U.S. Office Action dated Jan. 27, 2012 in related U.S. Appl. No. 12/468,277.

Extended European Search Report dated Aug. 26, 2009 in related European Application No. 09006723.2.

\* cited by examiner

FIG.9A
FIG.9B
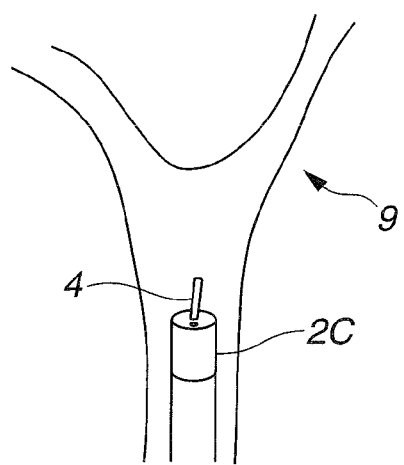
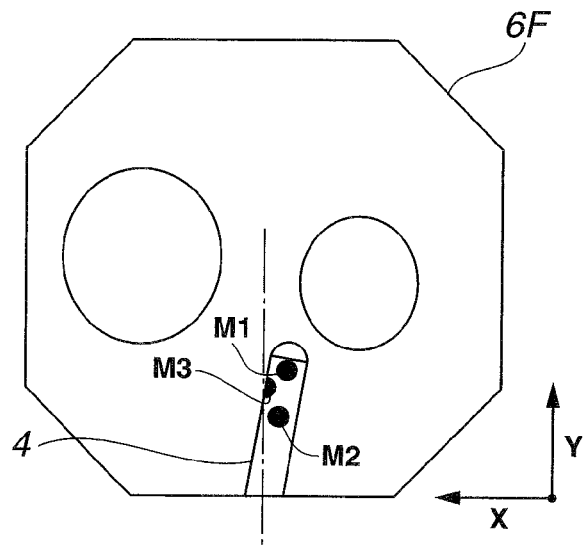
FIG.9C
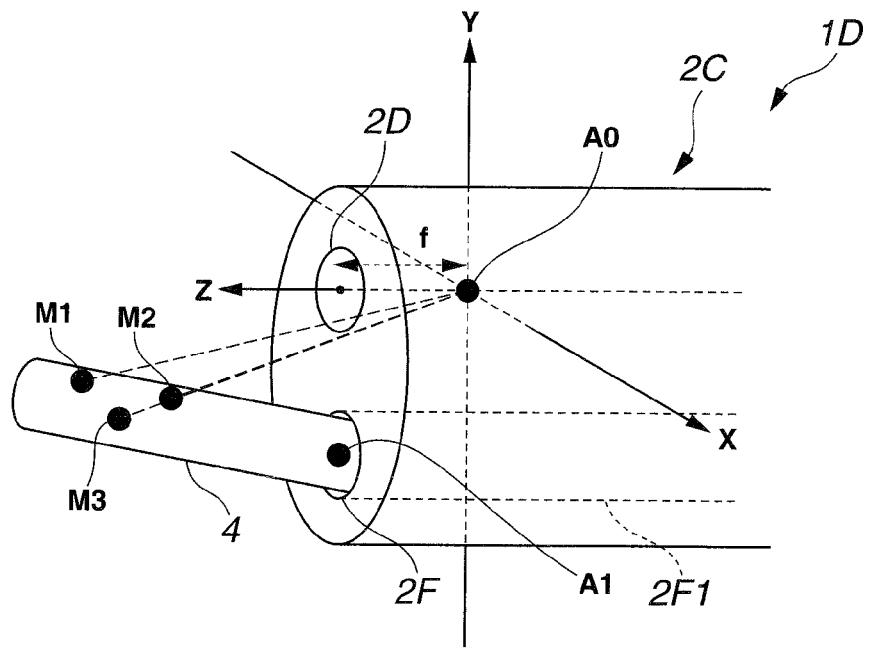

MEDICAL DEVICE

This application claims benefit of Japanese Application No. 2008-135633 filed in Japan on May 23, 2008, the contents of which are incorporated by this reference.

BACKGROUND OF THE INVENTION

1. Field of the Invention

The present invention relates to a medical device having an image pickup section that is able to pick up images of a tube cavity in a subject, more particularly, to a medical device that performs examination or treatment with high accuracy using virtual endoscopic images of a tube cavity based on three-dimensional image data of a subject.

2. Description of the Related Art

In recent years, diagnoses have been widely made using three-dimensional images. For example, a diagnosis for a target site can be made using three-dimensional image data of a subject which is obtained by picking up tomographic images of the subject with an X-ray CT (Computed Tomography) apparatus.

In the CT apparatus, a subject is continuously moved while X-ray radiating positions and detection positions are continuously rotated for continuous helical scanning of the subject (helical scan). The resulting continuous 2-dimensional tomographic images of the subject are used to create a three-dimensional image.

A three-dimensional image of bronchus of lungs is one type of the three-dimensional images used in diagnoses. Such a three-dimensional image of bronchus is used in a three-dimensional detection of the position of a diseased area with suspected lung cancer for example. In order to check the diseased area by a biopsy, a bronchus endoscope is inserted into the subject and a biopsy needle or biopsy forceps are extended out from a distal end portion of the endoscope, so as to collect tissue samples of the area.

In a tract such as bronchus in a body that is branched in multiple steps, in a case where a diseased area is located at the end of a bronchus, it is hard to bring the distal end of an insertion section of an endoscope to a position near the target site in a short period of time with accuracy. Thus, for example, Japanese Patent Application Laid-Open Publication No. 2004-180940 and Japanese Patent Application Laid-Open Publication No. 2005-131042 disclose navigation systems for insertion of endoscope in which a three-dimensional image of a tract in a subject is created based on image data of a three-dimensional area in the subject, and route along the tract to a target on the three-dimensional image is determined, so that virtual endoscopic images of the tract along the route can be created based on the image data.

SUMMARY OF THE INVENTION

A medical device of the present invention includes: an image pickup section that is able to pick up an image of a tube cavity in a subject; a medical instrument for examination or treatment in the tube cavity based on a reference point; a virtual endoscopic image generation section configured to generate a virtual endoscopic image in the tube cavity from a plurality of different line-of-sight positions using three-dimensional image data of the subject that is obtained in advance; an image retrieval section configured to retrieve the virtual endoscopic image highly similar to the endoscopic image of the tube cavity picked up by the image pickup section; a reference-point setting section configured to set a predetermined position near the image pickup section as the reference point based on the line-of-sight positions of the highly similar virtual endoscopic image; and a relative-position calculation section for calculating a relative position of the medical instrument to the reference point.

BRIEF DESCRIPTION OF THE DRAWINGS

FIG. 9A is a perspective view of a bronchus showing a treatment instrument that is protruded out of a treatment instrument port in the medical device according to a modified example 3 of the first embodiment;

FIG. 9B is an endoscopic image of a bronchus showing a treatment instrument that is protruded out of a treatment instrument port in the medical device according to the modified example 3 of the first embodiment;

FIG. 9C is a perspective view illustrating the relationship between a treatment instrument and a distal end portion thereof in bronchus to show a state where the treatment instrument is protruded out of a treatment instrument port in the medical device according to the modified example 3 of the first embodiment;

DETAILED DESCRIPTION OF THE PREFERRED EMBODIMENTS

First Embodiment

Now, with reference to the drawings, a medical device 1 of a first embodiment according to the present invention will be explained below.

Figure 1:
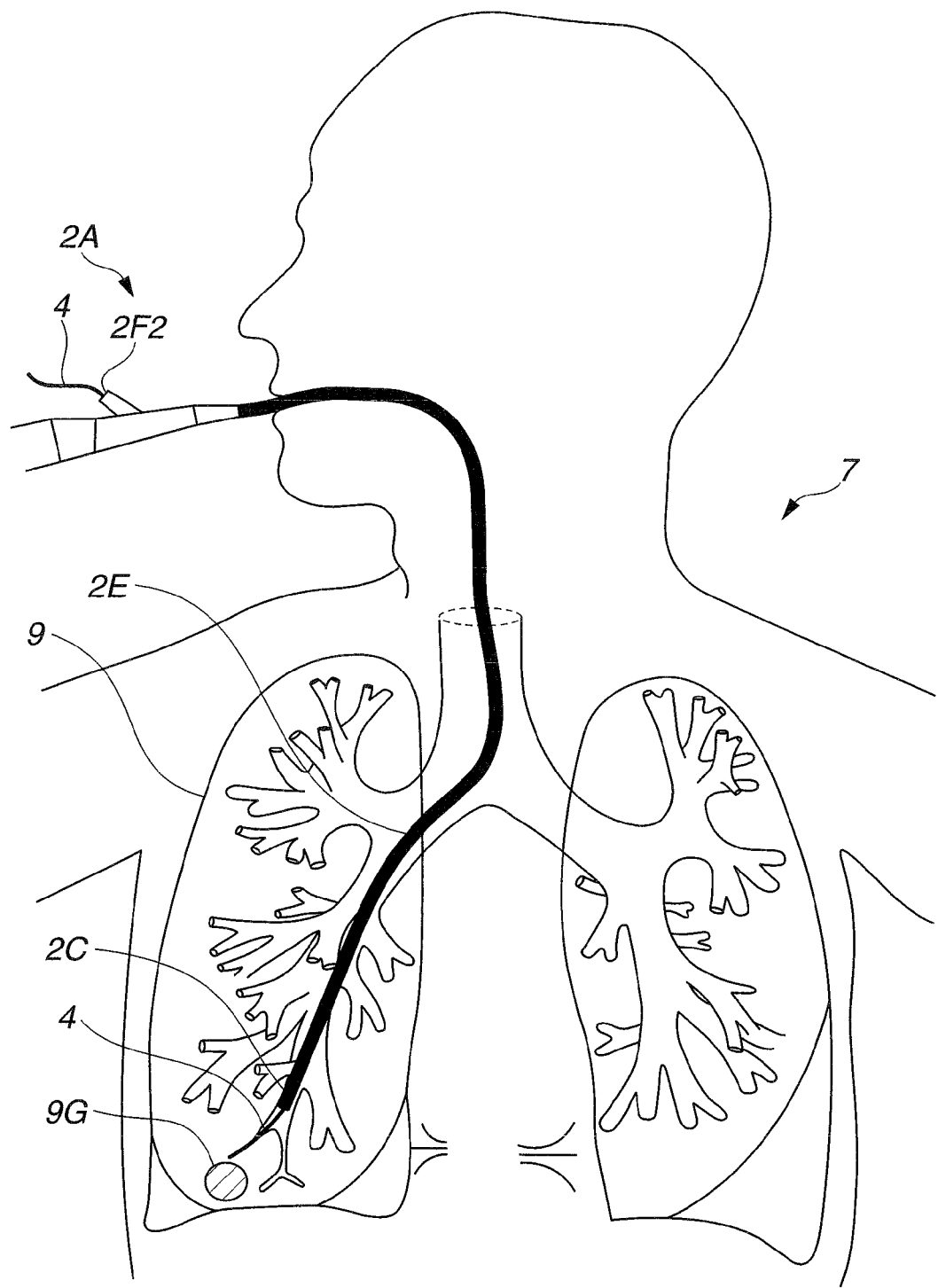
FIG. 1 is an illustrative view of a state in which an examination or treatment of a target site at a bronchus in a subject is being performed with a treatment instrument inserted through a channel of an endoscope.
Figure 2:
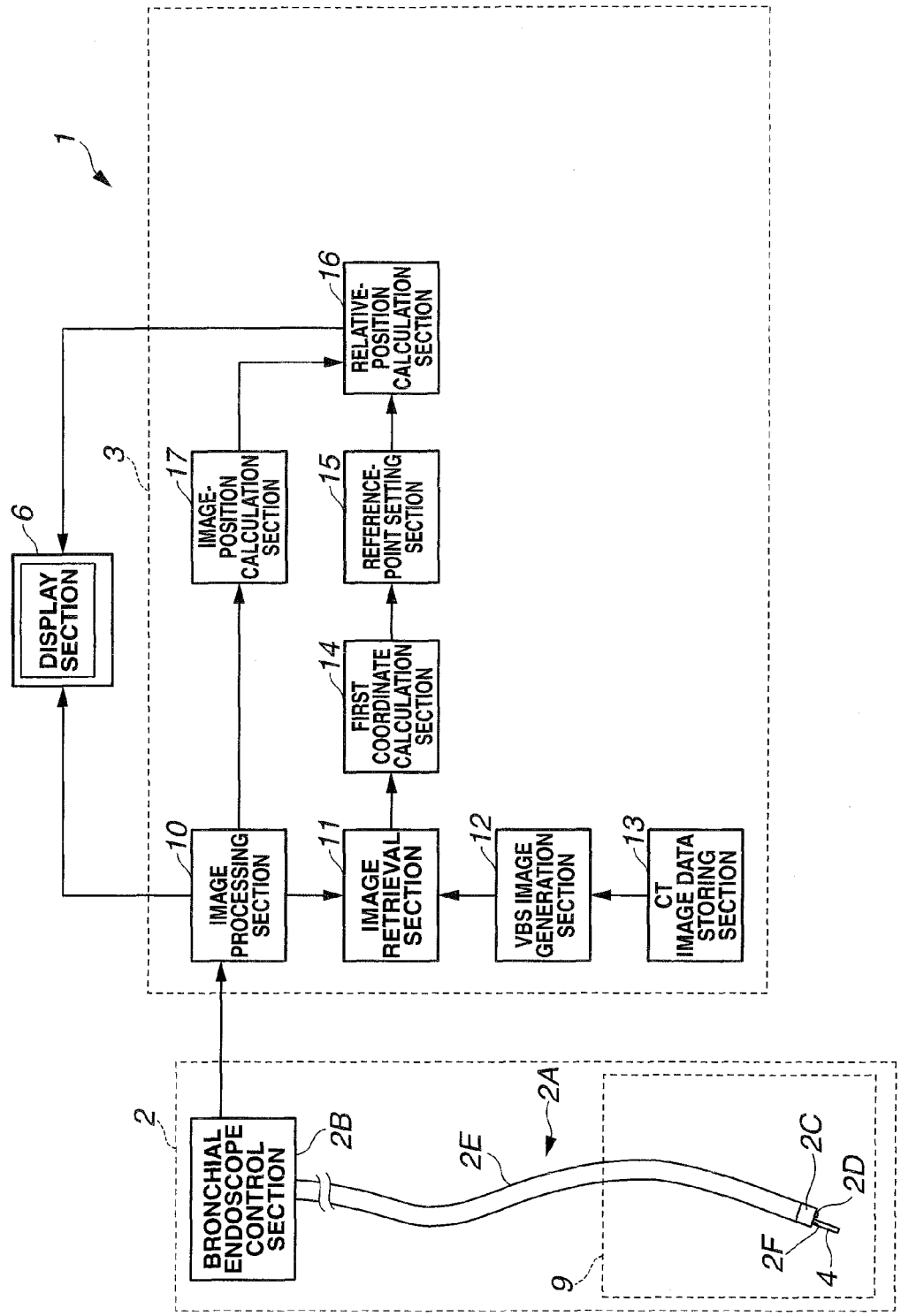
FIG. 2 is a configuration view showing a configuration of a medical device according to a first embodiment.

FIG. 1 is an illustrative view of a state in which an examination or treatment of a target site 9G at a bronchus 9 in a patient 7 with a medical instrument inserted through a channel 2F1 of an endoscope 2A is being performed, and FIG. 2 is a configuration view showing a configuration of the medical device 1 of an embodiment according to the present invention.

FIG. 1 shows a state where a distal end portion 2C of an insertion section 2E is being inserted into a tract having the minimal diameter for insertion of the distal end portion 2C in the bronchus 9. A treatment instrument 4 that is a medical instrument having a small diameter and is inserted through the channel 2F1 from a treatment instrument insertion port 2F2 is protruded out of the distal end portion 2C of the endoscope 2A, and samples the tissues of the target site 9G.

As shown in FIG. 1, the insertion section 2E of the endoscope 2A is narrow so as to be insertable into narrow bronchus tube cavities, and has a diameter on the order of 3 mm for example, but the treatment instrument 4 has a diameter on the order of 1 mm so as to be insertable into narrower end parts of the bronchus tube cavities. In many cases, the target site 9G at an end of a bronchus cannot be checked due to the narrowness by an image pickup section 2D arranged at the distal end portion 2C.

Next, as shown in FIG. 2, the medical device 1 having an insertion assist apparatus 3 of the present embodiment includes: an endoscope apparatus 2 configured to be inserted to the bronchus 9 that is a tube cavity in a body of the patient 7 who is the subject to pick up images of the inside of the bronchus 9 for a biopsy of the target site 9G at the end of the bronchus 9 (see FIG. 1); and the insertion assist apparatus 3.

The endoscope apparatus 2 is configured with an endoscope 2A having an image pickup section 2D such as a CCD arranged at the distal end portion 2C of the elongated insertion section 2E insertable through the bronchus 9 of the patient 7; an endoscope control section 2B configured to control the endoscope 2A; a display section 6; and the like. The insertion section 2E has a channel (not shown) formed therein through which the treatment instrument 4 as a medical instrument can be inserted, and the distal end portion 2C is provided with a liquid-supply port 2G as an opening and a treatment instrument port 2F of the channel, thereby as shown in FIGS. 1 and 2, the treatment instrument 4 can be protruded from the treatment instrument port 2F.

As shown in FIG. 2, the insertion assist apparatus 3 includes: an image processing section 10; a CT image data storing section 13; a VBS image generation section 12 configured to generate a virtual endoscopic image (Virtual Bronchus Scope Image: hereinafter, also referred to as "VBS image"); and an image retrieval section 11 configured to retrieve a virtual endoscopic image highly similar to an endoscopic image; a first coordinate calculation section 14; a reference-point setting section 15 configured to calculate a reference point based on a first coordinate point; an image-position calculation section 17; and a relative-position calculation section 16.

The image processing section 10 processes an endoscopic image (hereinafter, also referred to as "real image") picked up by the image pickup section 2D. The CT image data storing section 13 stores three-dimensional image data in a format such as DICOM (Digital Imaging and Communication in Medicine) that is generated by a known CT apparatus (not shown) for picking up X-ray tomographic images of the patient 7. The VBS image generation section 12 generates a VBS image from the image data in DICOM format based on line-of-sight parameters which will be explained later. The image-position calculation section 17 calculates the position of the treatment instrument 4 based on a real image, and the relative-position calculation section 16 calculates the position of the treatment instrument 4 relative to a reference point based on the information from the image-position calculation section 17 and the reference-point setting section 15.

The insertion assist apparatus 3 may include a VBS image storing section (not shown) for storing VBS images generated by the VBS image generation section 12.

The insertion assist apparatus 3 assists the insertion of the treatment instrument 4 inserted through the channel 2F1 to the target site 9G of the bronchus 9 in the patient 7 after the treatment instrument 4 is inserted to a position near the target site 9G at a tube cavity having the minimal diameter for insertion of the distal end portion 2C. The insertion assist apparatus 3 may be provided with a function of navigation system for insertion of the distal end portion 2C to a position near the target site 9G.

Figure 3:
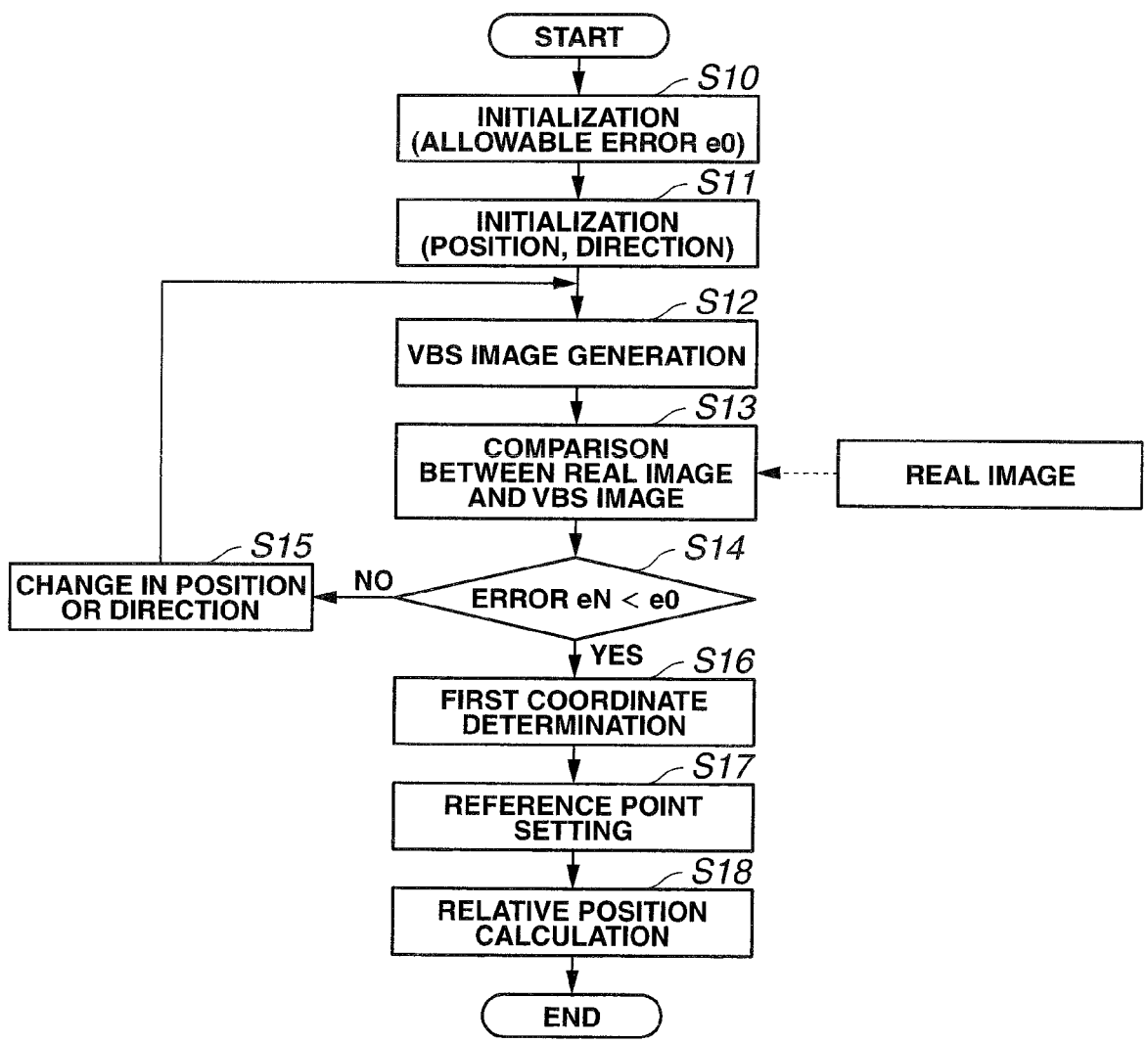
FIG. 3 is a flowchart illustrating a process flow of the medical device according to the first embodiment.

The insertion assist apparatus 3, first, retrieves a VBS image highly similar to a real image using the image retrieval section 11, and calculates the position and direction of the distal end portion 2C using the first coordinate calculation section 14. FIG. 3 is a flowchart illustrating a process flow of the insertion assist apparatus 3 for calculating the position and direction of the distal end portion 2C. According to the flowchart of FIG. 3, the process flow for calculating the position and direction of the distal end portion 2C of the endoscope 2A by the insertion assist apparatus 3 will be explained below.

<Step S10>

First, an allowable error e0 is set for determination of similarity which is performed by the image retrieval section 11. A smaller allowable error e0 allows the first coordinate calculation section 14 to more accurately calculate the position and direction of the distal end portion 2C, but takes a longer time. Thus, the allowable error e0 is changeable by a surgeon depending on the purpose.

<Step S11>

The VBS image generation section 12 generates a VBS image from a number of line-of-sight positions based on image data in DICOM format by changing six line-of-sight parameters. The parameters of line-of-sight positions as used herein are positions (x, y, z) and angles (θx, θy, θz). At Step S11, the initial values of the line-of-sight parameters that include the above six factors are set.

<Step S12>

The VBS image generation section 12 generates one VBS image using three-dimensional image data of bronchus 9 of the patient 7 stored in the CT image data storing section 13, based on the initial values of the line-of-sight parameters.

Alternatively, the VBS image generation section 12 may generate virtual endoscopic images at branches of the bronchus in advance from a plurality of different line-of-sight positions, and store the image in a VBS image storing section (not shown), so that the image retrieval section 11 can retrieve a VBS image most highly similar to a real image from the stored VBS images, and set the line-of-sight parameters of the most highly similar VBS image as initial values at the line-of-sight position which are used at Step S11.

<Step S13>

The image retrieval section 11 compares the real image and the VBS image generated by the VBS image generation section 12 on the similarity. The comparison between the images on the similarity is performed by a known image process which may be a matching process on the level of pixel data or a matching process on the level of features extracted from images. Because the matching process between the real image and the virtual endoscopic image is performed for every frame of the real image, the actual comparison is made based on the similarity between the static endoscopic image and the virtual endoscopic image. The matching process need not to be performed for all of the frames of the real image, but is repeated at appropriate intervals.

<Step S14 and Step S15>

When the error e calculated by the image retrieval section 11 for the similarity between the real image and the VBS image is larger than the allowable error e0 (No), at Step S15, the image retrieval section 11 outputs a line-of-sight parameter value of a little different position to the VBS image generation section 12. Then, at Step S12, the VBS image generation section 12 generates a next VBS image according to the new line-of-sight parameter set at Step S15.

The insertion assist apparatus 3 repeats the above loop operations, that is, outputs a different line-of-sight parameter, thereby the VBS image generated by the VBS image generation section 12 is gradually changed to an image similar to the real image, and the error e between the images becomes equal to the allowable error e0 or less (Yes) after the loop operations are repeated some times.

<Step S16>

When the similarity error e between the VBS image and the real image becomes equal to the allowable error e0 or less, the first coordinate calculation section 14 calculates the position (coordinate) and direction of the distal end portion 2C using the line-of-sight parameters of the VBS image having higher similarity.

Figure 4A:
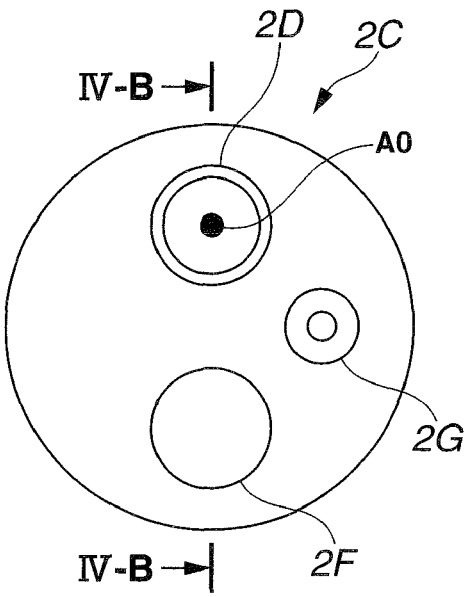
FIG. 4A is a schematic front view illustrating a configuration of a distal end portion of an endoscope in the medical device according to the first embodiment.
Figure 4B:
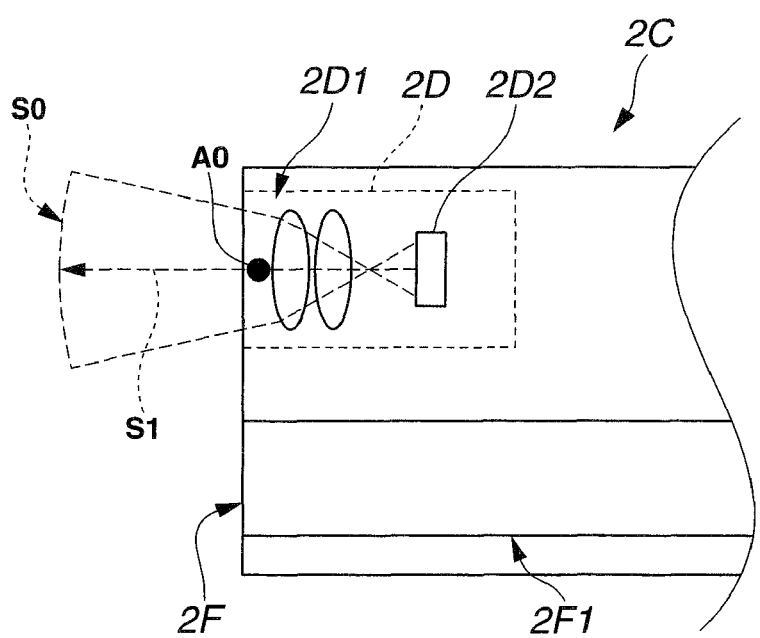
FIG. 4B is a schematic cross-sectional view taken along the IV-B-IV-B line of FIG. 4A.

Now, the structure of the distal end portion 2C will be explained below in more detail with FIG. 4A, FIG. 4B and FIG. 5. FIG. 4A is a schematic front view illustrating the configuration of the distal end portion 2C; FIG. 4B is a schematic cross-sectional view taken along the IV-B-IV-B line of FIG. 4A; and FIG. 5 is a schematic perspective view of the distal end portion 2C.

Figure 5:
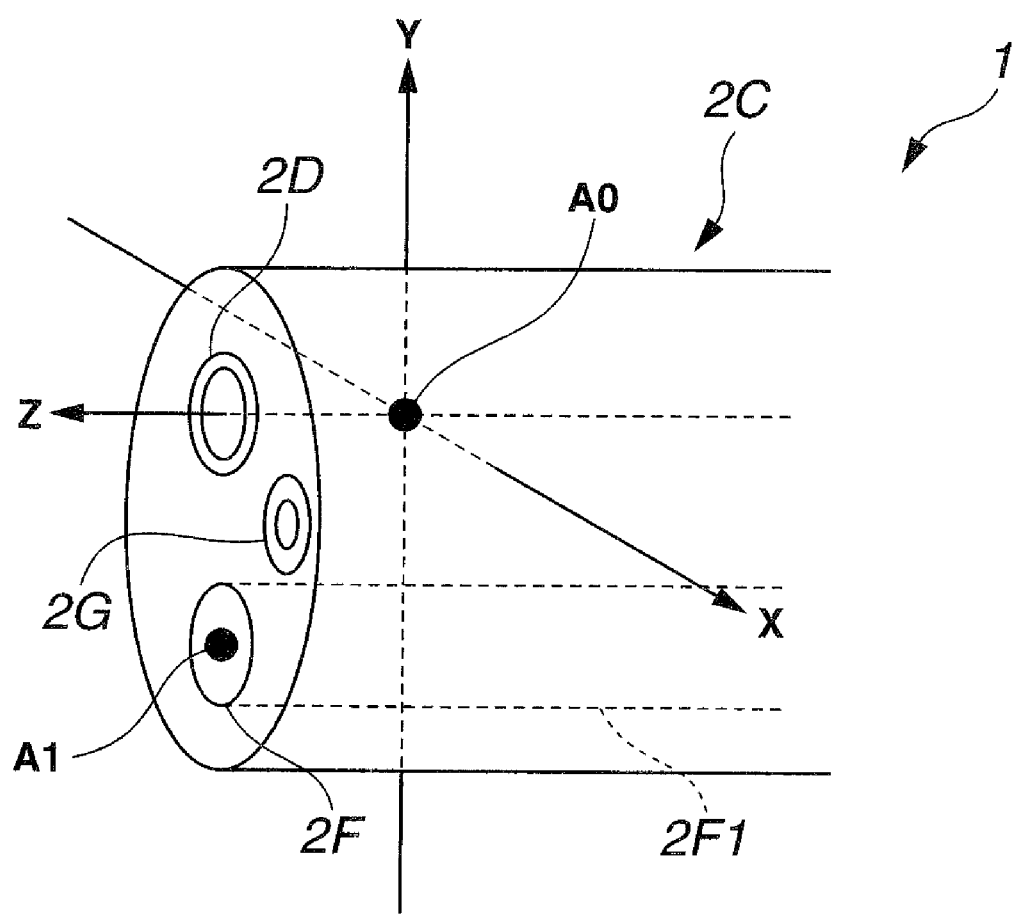
FIG. 5 is a schematic perspective view illustrating a configuration of a distal end portion of an endoscope in the medical device according to the first embodiment.

As shown in FIG. 4A, FIG. 4B and FIG. 5, the distal end portion 2C is provided with the treatment instrument port 2F of the channel 2F1, the image pickup section 2D, and the liquid-supply port 2G. The distal end portion 2C is further provided with an illumination section for illuminating the inside of tube cavity (not shown). The image pickup section 2D has an image pickup device 2D2 therein at the focus position of an optical system 2D1 to pick up an image within a field of view S0 in the direction with a line-of-sight S1 as a center.

The point on endoscope that corresponds to line-of-sight parameters of a VBS image shown by a first coordinate point calculated by the first coordinate calculation section 14 constitutes a pupil position A0 and the direction of the line-of-sight S1 as often called in an optical system.

Here, the coordinate of the first coordinate point A0 is expressed in a coordinate system of the virtual endoscopic image, in other words, a CT coordinate system, which means a lot to the medical device 1. That is, as already explained above, because the target site 9G for a biopsy is located at a bronchus end which the distal end portion 2C cannot reach, a surgeon cannot perform a biopsy and the like using the treatment instrument 4 while checking real images for the target site 9G. Therefore, a surgeon performs a biopsy based on the position of the target site 9G shown in a CT coordinate system in the three-dimensional image data that is obtained by CT in advance. However, the position of the distal end portion 2C and the position of the treatment instrument 4 for the biopsy protruded from the distal end portion 2C can be checked only in an endoscope coordinate system based on the distal end portion 2C which has no relationship with the CT coordinate system.

To the contrary, in the insertion assist apparatus 3, the coordinate of the first coordinate point A0 on a part of the distal end portion 2C that is close to the target site 9G is expressed in the same CT coordinate system, which allows the surgeon to use the coordinate to bring the treatment instrument 4 to the target site 9G for a biopsy and the like. The examination or treatment performed using the medical device 1 herein may be spray of medication, biopsy, mucus sampling, extraction of foreign object, high-frequency cauterization, or the like.

The endoscope coordinate system for the medical device 1 shown in FIG. 5 is not the same with the CT coordinate system, but is a coordinate system which is processed to correspond to the CT coordinate system by the insertion assist apparatus 3, in other words, a coordinate system which can be transformed into the CT coordinate system by a coordinate transformation process.

<Step S17>

In the insertion assist apparatus 3, the reference-point setting section 15 sets a position at a part near the image pickup section 2D as a reference point based on the first coordinate point A0. The part near the image pickup section 2D is in the bronchus that is a tube cavity in a body of the patient 7 who is the subject, and includes the inside of the image pickup section 2D. The position near the image pickup section 2D is preferably in the bronchus between the position A0 on the line-of-sight of the image pickup section 2D and the target site 9G, more preferably a predetermined position on the distal end portion 2C.

FIG. 5 shows an example in which the reference point A1 is set in the treatment instrument port 2F, more specifically at the center of the treatment instrument port 2F. That is, the reference point A1 is set in the treatment instrument port 2F that serves as a starting point from which the treatment instrument 4 is protruded.

<Step S18>

Figure 6A:
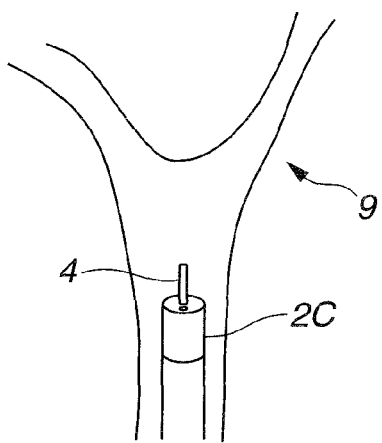
FIG. 6A is a perspective view of a bronchus showing a treatment instrument that is protruded out of a treatment instrument port in the medical device according to the first embodiment.
Figure 6B:
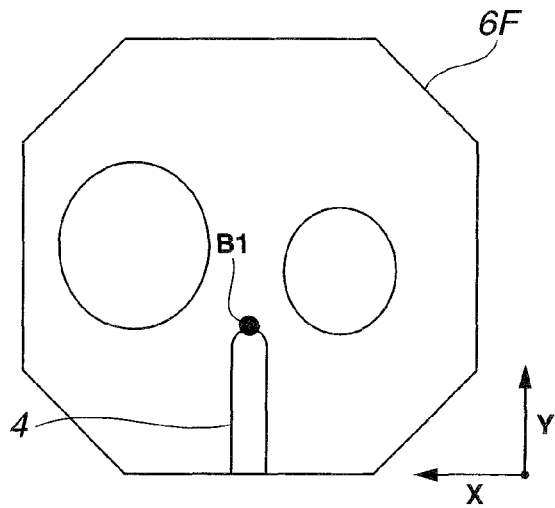
FIG. 6B is an endoscopic image of a bronchus showing a treatment instrument that is protruded out of a treatment instrument port in the medical device according to the first embodiment.
Figure 6C:
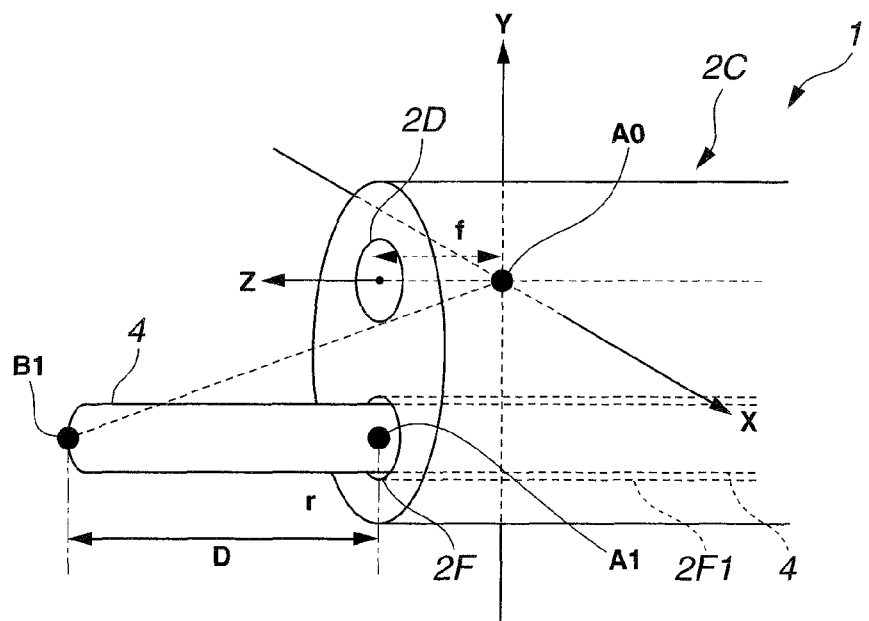
FIG. 6C is a perspective view illustrating the relationship between a treatment instrument and a distal end portion thereof in bronchus to show a state where the treatment instrument is protruded out of a treatment instrument port in the medical device according to the first embodiment.

The treatment instrument 4 is inserted into the channel 2F1 from the treatment instrument insertion port 2F2 on the proximal end side of the endoscope 2A, and is protruded out of the treatment instrument port 2F of the distal end portion 2C. FIGS. 6A to 6C are illustrative views showing the state with the treatment instrument 4 being protruded out of the treatment instrument port 2F: FIG. 6A is a perspective view showing inside of the bronchus 9; FIG. 6B shows an endoscopic image; and FIG. 6C is a perspective view illustrating the relationship between the treatment instrument 4 and the distal end portion 2C.

At Step S18, the image-position calculation section 17 calculates a coordinate position (Xd, Yd) for the distal end position B1 of the treatment instrument 4 in the endoscopic image 6F shown in FIG. 6B. The Y-axis in the XY coordinate system shown in FIG. 6B corresponds to the Z-axis in the XYZ coordinate system shown in FIG. 6C.

The relative-position calculation section 16 calculates the relationship between the reference point A1 calculated by the reference-point setting section 15 and the distal end position B1 of the treatment instrument 4 calculated by the image-position calculation section 17.

In the example shown in FIGS. 6A to 6C, the treatment instrument 4 is straightly protruded from the treatment instrument port 2F. In the case, the position (Xp, Yp, Zp) of the distal end position B1 can be calculated as follows using the position of the treatment instrument port 2F, that is the reference point A1 (Xc, Yc, Zc), and the coordinate (Xd, Yd, f) of the distal end position B1 of the treatment instrument 4 calculated using the endoscopic image 6F:

$$(Xp, Yp, Zp) = (Xc, Yc, Ycf/yd)$$

Therefore, a correction value ($\Delta x$, $\Delta y$, $\Delta z$) can be calculated using the following formula with the position (Xp, Yp, Zp) of the treatment instrument in the CT coordinate system based on the endoscope apparatus 2 and the position (Xus, Yus, Zus) of the treatment instrument based on the treatment instrument 4:

$$(\Delta x, \Delta y, \Delta z) = (Xp, Yp, Zp) - (Xus, Yus, Zus)$$

The insertion assist apparatus 3 is able to calculate a relative position used to accurately transform the position of the treatment instrument 4 to the CT coordinate system. This allows the medical device 1 to perform an examination or treatment with high positional accuracy using the treatment instrument 4 inserted through the channel 2F1 of the endoscope 2A.

Modified Example 1 of First Embodiment

Figure 7A:
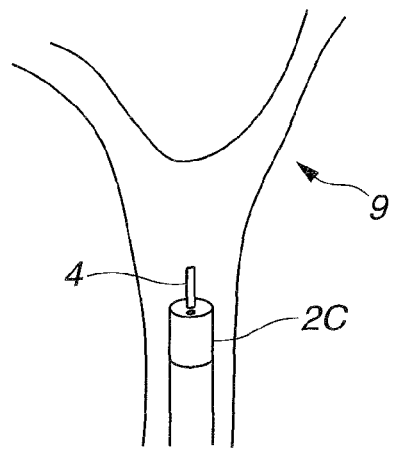
FIG. 7A is a perspective view of a bronchus showing a treatment instrument that is protruded out of a treatment instrument port in the medical device according to a modified example 1 of the first embodiment.
Figure 7B:
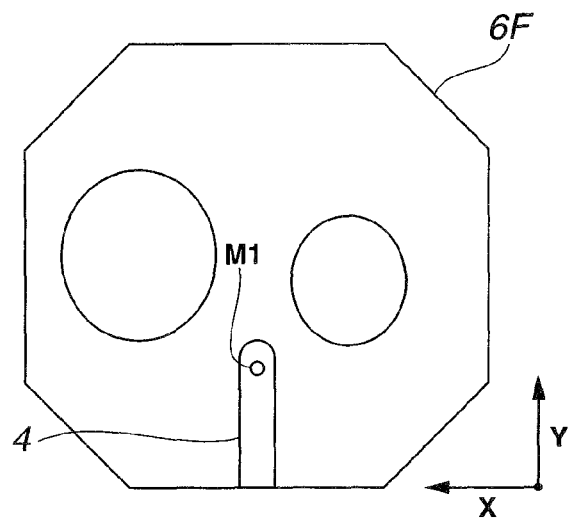
FIG. 7B is an endoscopic image of a bronchus showing a treatment instrument that is protruded out of a treatment instrument port in the medical device according to the modified example 1 of the first embodiment.
Figure 7C:
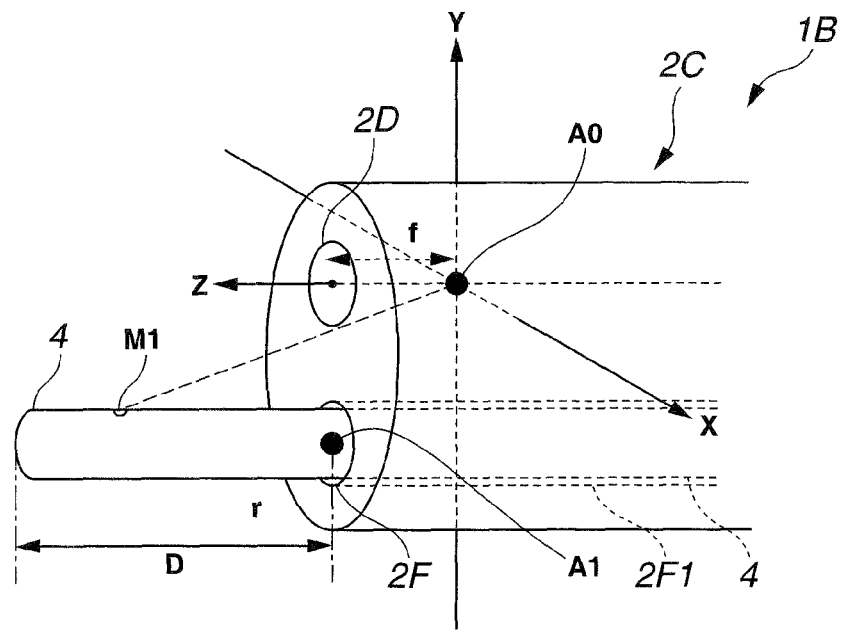
FIG. 7C is a perspective view illustrating the relationship between a treatment instrument and a distal end portion thereof in bronchus to show a state where the treatment instrument is protruded out of a treatment instrument port in the medical device according to the modified example 1 of the first embodiment.

FIGS. 7A to 7C are illustrative views showing a method for calculating a relative position between the reference point A1 and the treatment instrument 4 in a medical device 1B according to a modified example 1 of the first embodiment: FIG. 7A is a perspective view showing inside of the bronchus 9; FIG. 7B shows an endoscopic image; and FIG. 7C is a perspective view illustrating the relationship between the treatment instrument 4 and the distal end portion 2C. The medical device 1B is similar to the medical device 1, and the same components thereof are denoted by the same reference numerals, which will not be explained below.

As shown in FIG. 7B and FIG. 7C, the medical device 1B is provided with a marker M1 arranged at the distal end portion of the treatment instrument 4 in advance. The marker M1 is preferably arranged at a position which is in the up direction when the medical device 1B is bended, so that the position of the marker M1 can be easily checked in an endoscopic image.

Due to the marker M1 arranged at a predetermined position on the treatment instrument 4, the image-position calculation section 17 of the medical device 1B is able to more easily and more accurately detect the position of the treatment instrument 4 than in the case with the medical device 1. Thus, the medical device 1B provides more accurate examination and the like, in addition to the effect provided by the medical device 1.

The marker M1 may be a point, a line segment, a circle, an oval, or a square, and an endpoint of the line segment or the center of the circle may be automatically extracted by an image detection process. In addition, the marker may have a color such as blue and green which is different from the site in bronchus tube cavity to enhance the detection sensitivity of the marker.

Modified Example 2 of First Embodiment

Figure 8A:
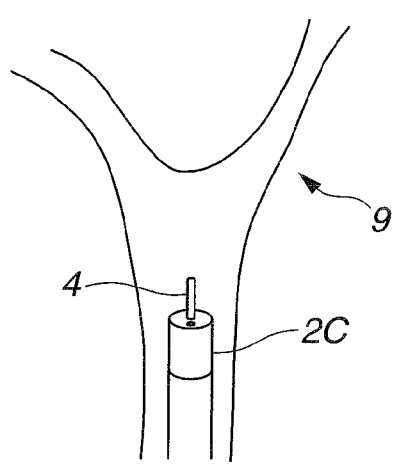
FIG. 8A is a perspective view of a bronchus showing a treatment instrument that is protruded out of a treatment instrument port in the medical device according to a modified example 2 of the first embodiment.
Figure 8B:
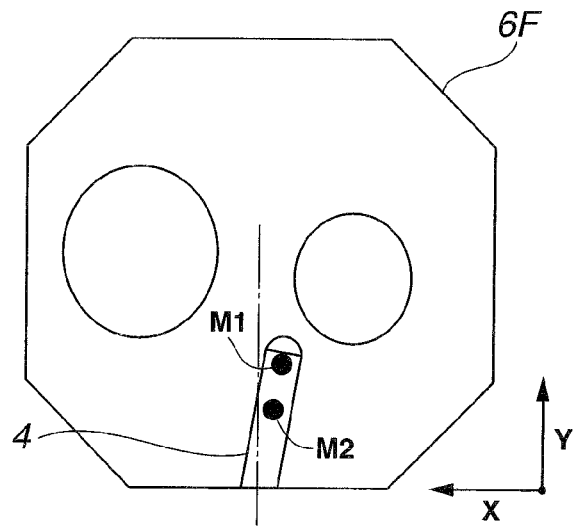
FIG. 8B is an endoscopic image of a bronchus showing a treatment instrument that is protruded out of a treatment instrument port in the medical device according to the modified example 2 of the first embodiment.
Figure 8C:
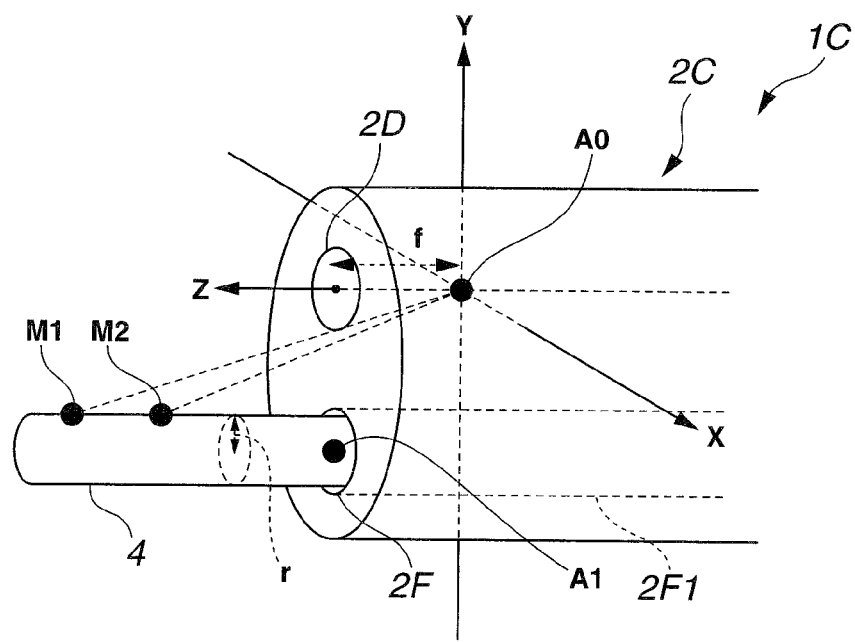
FIG. 8C is a perspective view illustrating the relationship between a treatment instrument and a distal end portion thereof in bronchus to show a state where the treatment instrument is protruded out of a treatment instrument port in the medical device according to the modified example 2 of the first embodiment.

FIGS. 8A to 8C are illustrative views showing a method for calculating a relative position between the reference point A1 and the treatment instrument 4 in a medical device 1C according to a modified example 2 of the first embodiment: FIG. 8A is a perspective view showing inside of the bronchus 9; FIG. 8B shows an endoscopic image; and FIG. 8C is a perspective view illustrating the relationship between the treatment instrument 4 and the distal end portion 2C. The medical device 1C is similar to the medical devices 1 and 1B, and the same components thereof are denoted by the same reference numerals, which will not be explained below.

As shown in FIG. 8B and FIG. 8C, the medical device 1C is provided with two markers M1 and M2 arranged on the center line of the distal end portion of the treatment instrument 4 in advance. The medical device 1C having the treatment instrument 4 with two markers M1 and M2 is able to calculate the relative position of the treatment instrument 4 to the reference point A1 even when the treatment instrument 4 curves to the direction of X-axis or Z-axis after protruded from treatment instrument port 2F, that is even when the marker is positioned on the X-Z plane.

Now, detail explanation will be provided below with reference to FIG. 8C. The vectors from the viewpoint position A0 to each of the markers M1 and M2 can be expressed by the following Formula 1 and Formula 2 with constants n1 and n2, respectively:

$$\vec{A} = n1\vec{a}$$ [Formula 1]

$$\vec{B} = n2\vec{b}$$ [Formula 2]

The position moved in the Y-axis direction from the treatment instrument port 2F by r that corresponds to the radius of the treatment instrument 4 can be expressed as (Xc, Yc−r, Zc), and this position and the two markers M1 and M2 are positioned on the same straight line, which provides the following Formula 3, a linear equation:

$$\begin{pmatrix} Xc \\ Yc \\ Zc \end{pmatrix} = \begin{pmatrix} n1a_x + (n2b_x - n1a_x)t \\ n1a_y + (n2b_y - n1a_y)t \\ n1a_z + (n2b_z - n1a_z)t \end{pmatrix}$$ [Formula 3]

wherein $$\vec{a} = \begin{pmatrix} a_x \\ a_y \\ a_z \end{pmatrix} = \begin{pmatrix} xd1/\sqrt{xd1^2 + yd1^2 + f^2} \\ yd1/\sqrt{xd1^2 + yd1^2 + f^2} \\ f/\sqrt{xd1^2 + yd1^2 + f^2} \end{pmatrix}$$ [Formula 4]

and $$\vec{b} = \begin{pmatrix} b_x \\ b_y \\ b_z \end{pmatrix} = \begin{pmatrix} xd2/\sqrt{xd2^2 + yd2^2 + f^2} \\ yd2/\sqrt{xd2^2 + yd2^2 + f^2} \\ f/\sqrt{xd2^2 + yd2^2 + f^2} \end{pmatrix}$$ [Formula 5]

and wherein the vector a and the vector b are unit vectors for vector A and vector B, respectively.

Moreover, it is known that the marker M1 is separated from the marker M2 by a distance d, which results in the following Formula 6:

$$d = \sqrt{(n2b_x - n1a_x)^2 + (n2b_y - n1a_y)^2 + (n2b_z - n1a_z)^2}$$ [Formula 6]

Assuming that the two markers and the point (Xc, Yc+dy, Zc) are positioned on the plane orthogonal to the X-Z plane, the inner product is calculated to be 0, resulting in the following Formula 7:

$$\frac{(Yc - r - n1a_y) \cdot 1}{\sqrt{(Xc - n1a_x)^2 + (Yc - r - n1a_y)^2 + (Zc - n1a_z)^2}} =$$ [Formula 7]

$$\frac{(Yc - r - n2b_y) \cdot 1}{\sqrt{(Xc - n2b_x)^2 + (Yc - r - n2b_y)^2 + (Zc - n2b_z)^2}}$$

The above Formula 3, Formula 6, and Formula 7 are used to calculate the values of n1, n2, and t, which leads to the calculation of the relative position and direction of the distal end portion 2C.

The medical device 1C of the present embodiment provides an advantage, in addition to the effects provided by the medical device 1 and the like, that a relative position of the treatment instrument 4 to be accurately transformed to a CT coordinate system can be calculated even when the treatment instrument 4 is protruded from the treatment instrument port 2F in a tilted direction because the two markers are arranged to the treatment instrument 4.

Modified Example 3 of First Embodiment

FIGS. 9A to 9C are illustrative views showing a method for calculating a relative position between the reference point A1 and the treatment instrument 4 in a medical device 1D according to a modified example 3 of the first embodiment: FIG. 9A is a perspective view showing inside of the bronchus 9; FIG. 9B shows an endoscopic image; and FIG. 9C is a perspective view illustrating the relationship between the treatment instrument 4 and the distal end portion 2C. The medical device 1D is similar to the medical devices 1 and the like, and the same components thereof are denoted by the same reference numerals, which will not be explained below.

As shown in FIG. 9B and FIG. 9C, the medical device 1D is provided with three markers M1, M2 and M3 that are arranged at the distal end portion of the treatment instrument 4 but are not on the same straight line. In the case, the vectors from viewpoint position A0 to each marker can be expressed by the following formulas with constants n1, n2, and n3, respectively:

$$\vec{A} = n1\vec{a}$$ [Formula 8]

$$\vec{B} = n2\vec{b}$$ [Formula 9]

$$\vec{C} = n3\vec{c}$$ [Formula 9]

wherein $$\vec{a} = \begin{pmatrix} a_x \\ a_y \\ a_z \end{pmatrix} = \frac{1}{\sqrt{xd1^2 + yd1^2 + f^2}} \begin{pmatrix} xd1 \\ yd1 \\ f \end{pmatrix}$$ [Formula 11]

$$\vec{b} = \begin{pmatrix} b_x \\ b_y \\ b_z \end{pmatrix} = \frac{1}{\sqrt{xd2^2 + yd2^2 + f^2}} \begin{pmatrix} xd2 \\ yd2 \\ f \end{pmatrix}$$ [Formula 12]

$$\vec{c} = \begin{pmatrix} c_x \\ c_y \\ c_z \end{pmatrix} = \frac{1}{\sqrt{xd3^2 + yd3^2 + f^2}} \begin{pmatrix} xd3 \\ yd3 \\ f \end{pmatrix}$$ [Formula 13]

Because each distance between the markers is known, the distances d1, d2, and d3 can be expressed as follows:

$$d_{12}^2 = (a_x - b_x)^2 + (a_y - b_y)^2 + (a_z - b_z)^2$$

$$d_{23}^2 = (b_x - c_x)^2 + (b_y - c_y)^2 + (b_z - c_z)^2$$

$$d_{31}^2 = (c_x - a_x)^2 + (c_y - a_y)^2 + (c_z - a_z)^2$$

The values of n1, n2, and n3 in Formula 8 to Formula 10 can be obtained by solving the above simultaneous equations, which leads to the calculation of the relative positions and directions of the marker M1, M2, and M3 on the treatment instrument 4 to a first coordinate point A0. Thus, the medical device 1D is able to calculate the position of the distal end portion B1 and the like of the treatment instrument 4 based on a CT coordinate system.

The medical device 1D of the present embodiment provides an advantage, in addition to the effects provided by the medical device 1 and the like, that a relative position of the treatment instrument 4 to be accurately transformed to a CT coordinate system can be calculated even when the treatment instrument 4 is protruded from the treatment instrument port 2F in a three-dimensionally tilted direction, using the treatment instrument 4 having three markers arranged thereon.

Second Embodiment

Figure 10:
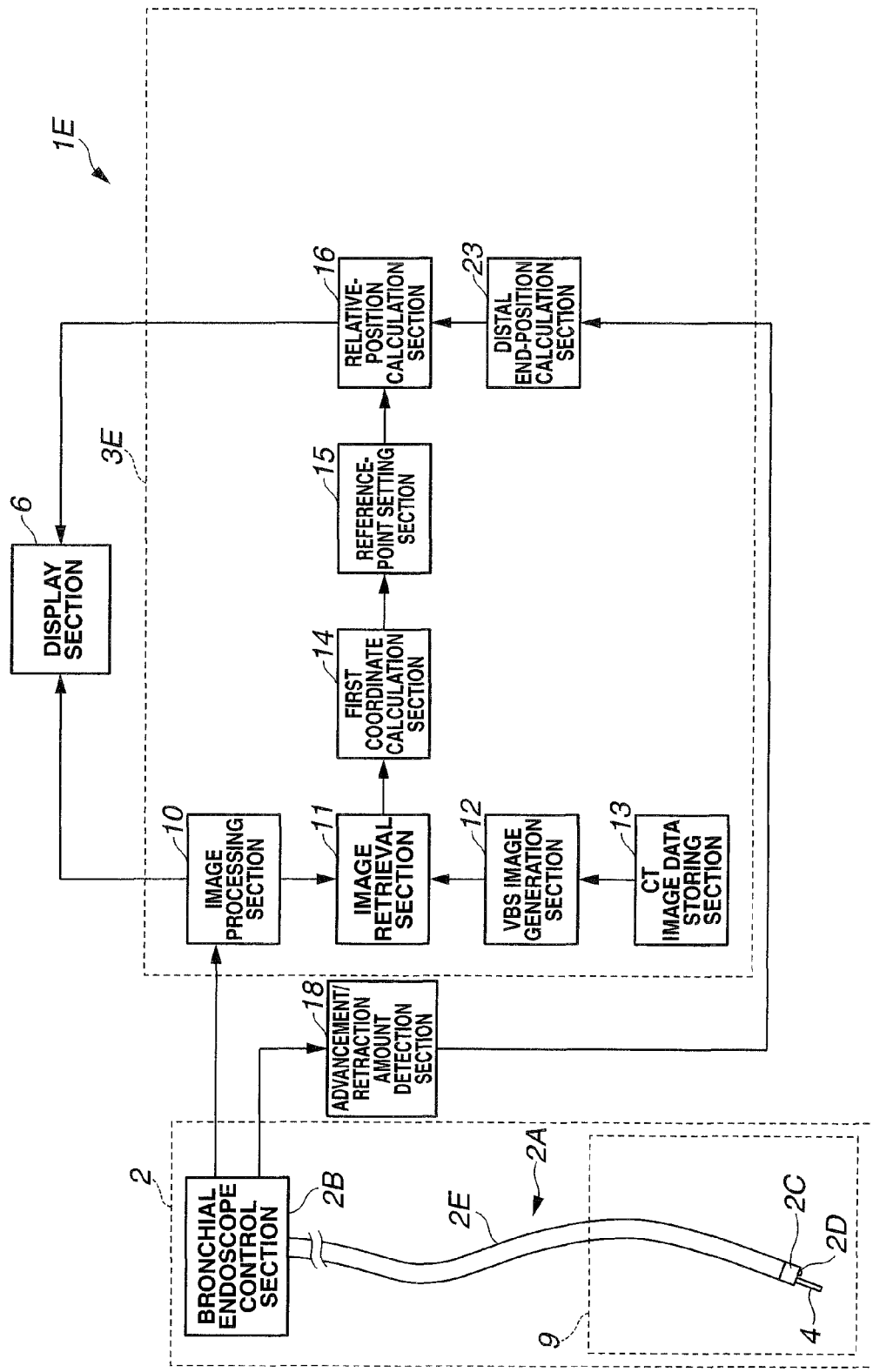
FIG. 10 is a configuration view showing a configuration of a medical device according to a second embodiment.

Now, with reference to the drawings, a medical device 1E of a second embodiment according to the present invention will be explained below. The medical device 1E is similar to the medical device 1 and the like, and the same components thereof are denoted by the same reference numerals, which will not be explained below. FIG. 10 is a configuration view showing a configuration of the medical device 1E of the embodiment according to the present invention.

As shown in FIG. 10, the medical device 1E includes: an advancement/retraction amount detection section 18 configured to detect an amount of advancement/retraction of the treatment instrument 4; and a distal end-position calculation section 23 configured to calculate a distal end position of the treatment instrument 4. As shown in FIG. 1, the treatment instrument 4 is inserted into the channel 2F1 from the treatment instrument insertion port 2F2 on the proximal end side of the endoscope 2A, and is protruded from the treatment instrument port 2F of the distal end portion 2C.

The length of the channel 2F1 is known. Thus, the distal end-position calculation section 23 of the medical device 1E is able to calculate the distal end position of the treatment instrument 4 and the distance D of the treatment instrument 4 protruded from the treatment instrument port 2F by detecting the length of the treatment instrument 4 inserted from the treatment instrument insertion port 2F2 using the advancement/retraction amount detection section 18.

Moreover, in the medical device 1E the relative-position calculation section 16 is able to calculate a relative position that is used to accurately transform the distal end position of the treatment instrument 4 to a CT coordinate system, based on the distal end position of the treatment instrument 4 calculated by the distal end-position calculation section 23 and the reference point.

Figure 11A:
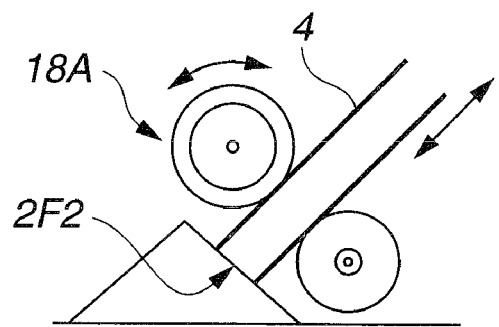
FIGS. 11A to 11C are illustrative views of specific examples of an advancement/retraction amount detection section in the medical device according to the second embodiment.
Figure 11B:
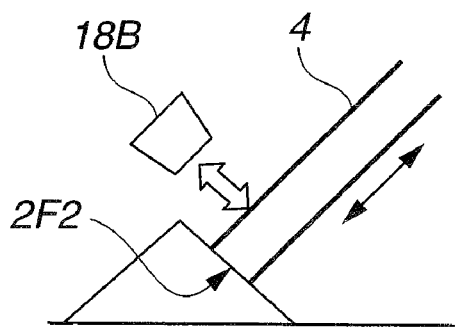
Figure 11C:
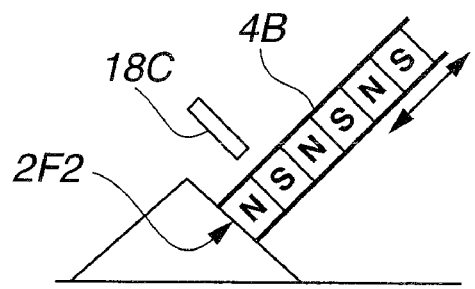

FIGS. 11A to 11C are illustrative views of specific examples of the advancement/retraction amount detection section 18: FIG. 11A shows an encoder 18A as one example of the advancement/retraction amount detection section 18 that is arranged near the treatment instrument insertion port 2F2; FIG. 11B shows an optical detector 18B for the detection; and FIG. 11C shows a magnetic sensor 18C for the detection.

The encoder 18A includes a rotary section in contact with the treatment instrument 4 that rotates in response to an advancement/retraction of the treatment instrument 4, so as to detect the amount of advancement/retraction of the treatment instrument 4. The optical detector 18B detects a movement, that is, an amount of advancement/retraction of the treatment instrument 4 by using infrared ray or laser. The magnetic sensor 18C detects a movement, that is, an amount of advancement/retraction of the treatment instrument 4 based on a magnetic scale arranged at a treatment instrument 4B.

FIGS. 11A to 11C show examples in which sensors as the advancement/retraction amount detection section 18 are arranged at the treatment instrument insertion port 2F2, but the sensors may be arranged at the main body of the endoscope 2A such as the operation section thereof, or at the treatment instrument 4.

Figure 12A:
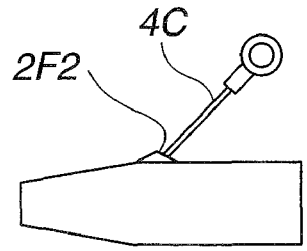
FIGS. 12A to 12C are illustrative views of specific examples of an advancement/retraction amount detection section in the medical device according to the second embodiment.
Figure 12B:
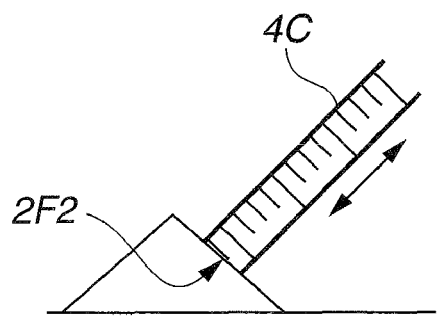
Figure 12C:
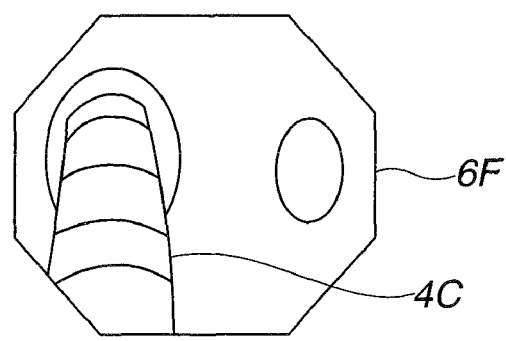

Next, the advancement/retraction amount detection section 18 using an image-position detection section (not shown) will be explained below. FIGS. 12A to 12C are views illustrating the advancement/retraction amount detection section 18 using the image-position detection section: FIG. 12A is a schematic view of the treatment instrument insertion port 2F2 seen from the lateral direction thereof; FIG. 12B is an enlarged view showing the area near the treatment instrument insertion port 2F2 of FIG. 12A; and FIG. 12C shows an endoscopic image 6F.

As shown in FIG. 12B and FIG. 12C, a treatment instrument 4C is provided with a scale, and the scale of the treatment instrument 4C can be recognized also in the endoscopic image 6F. So, the image-position detection section is able to detect an amount of advancement/retraction of the treatment instrument 4C by detecting an advancement/retraction of the scale on the treatment instrument 4C in the endoscopic image 6F. In other words, in the insertion assist apparatus having the treatment instrument 4C shown in FIGS. 12A to 12C, the image-position detection section functions as the advancement/retraction amount detection section 18.

Figure 13A:
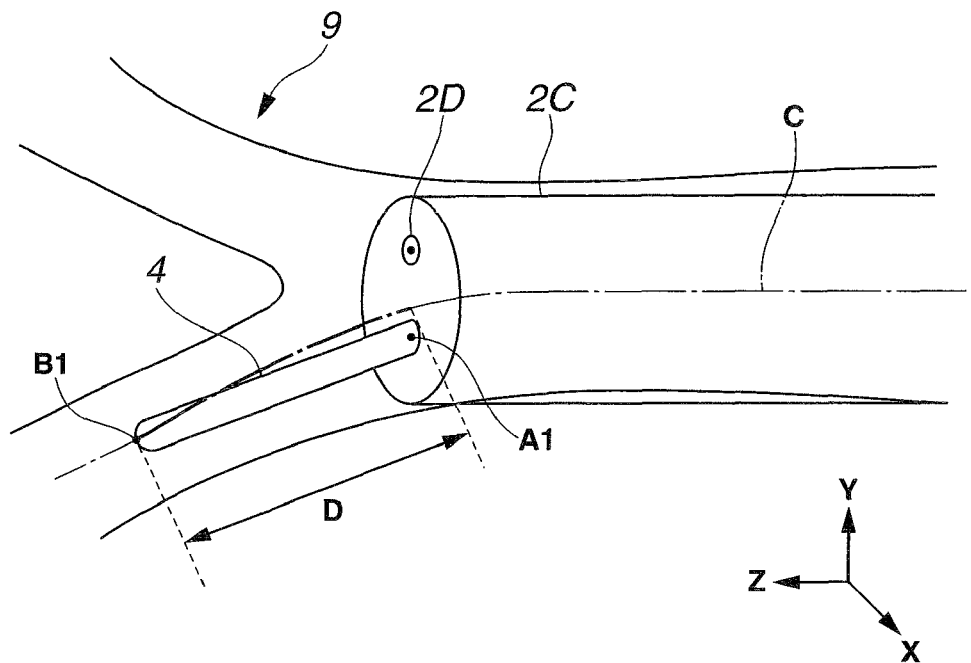
FIG. 13A is a schematic perspective view illustrating the relationship between an amount of advancement/retraction of the treatment instrument and the distal end position thereof in the medical device according to the second embodiment in a case where centerline information is used.
Figure 13B:
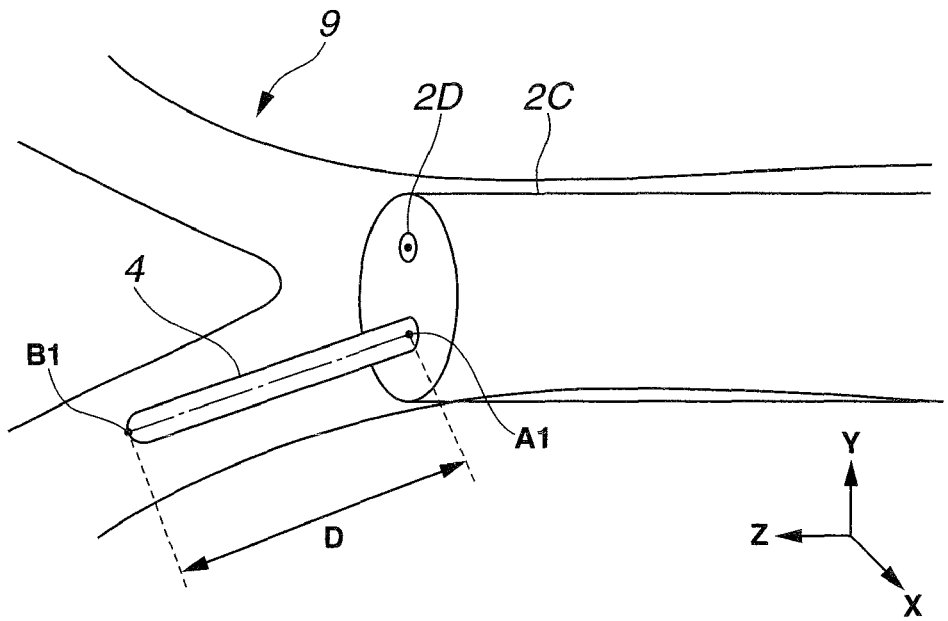
FIG. 13B is a schematic perspective view of the relationship between an amount of advancement/retraction of the treatment instrument and the distal end position thereof in the medical device according to the second embodiment in a case where directional information of the treatment instrument is used.

Next, the relationship between an amount of advancement/retraction D of the treatment instrument 4 and the position of the distal end of the treatment instrument 4 will be explained below with FIGS. 13A and 13B. FIGS. 13A and 13B are schematic perspective views illustrating the relationship between an amount of advancement/retraction of the treatment instrument 4 and the position of the distal end of the treatment instrument 4: FIG. 13A shows a case in which centerline information is used; and FIG. 13B shows a case in which directional information of the treatment instrument is used.

Here, simple representations of a state of a branch of a tube cavity, a length to each branch, and the like based on three-dimensional image data of the bronchus 9 are important to increase the process speed of the insertion assist apparatus. Thus, the insertion assist apparatus 3E uses the concept of "centerline and volume". The centerline is the line connecting the points of the center of gravity of the plane of a tube cavity that are orthogonal to the longitudinal direction, while the volume is the information showing the position of a tube wall in the tube cavity.

In FIG. 13A, for an amount of advancement/retraction D of the treatment instrument 4, the distal end-position calculation section 23 calculates the position of the treatment instrument 4 on the assumption that the treatment instrument 4 moves along the centerline C. The actual route of the movement of the distal end B1 of the treatment instrument 4 is different from the centerline C, but at the end of a tube cavity of bronchus 9, the above approximation does not cause a large error. The use of centerline information allows the distal end-position calculation section 23 to process a movement of the treatment instrument 4 by a simple calculation, which increases the speed of the process.

To the contrary, FIG. 13B shows an example in which, for an amount of advancement/retraction D of the treatment instrument 4, the position of the treatment instrument 4 is calculated by the distal end-position calculation section 23 on the assumption that the treatment instrument 4 moves straight forward. The route of the movement of the distal end B1 of the treatment instrument 4 may be a curved line, but at the end of a tube cavity of bronchus 9, the approximation does not cause a large error. The approximation for the straight movement of the treatment instrument 4 allows the distal end-position calculation section 23 to process the movement of the treatment instrument 4 by a simple calculation, which increases the speed of the process.

The medical device 1E of the present embodiment provides an advantage, in addition to the effects provided by the medical device 1 and the like of the first embodiment, that the distal end position of the treatment instrument 4 can be calculated based on an amount of advancement/retraction D and the position of the reference point A1 while the medical device 1 and the like cannot detect the distal end position B1 of the treatment instrument 4 when the position of the marker and the like cannot be detected using an endoscopic image.

In the above explanation, because the length of the channel 2F1 is known, the protruded amount D of the treatment instrument 4 from the treatment instrument port 2F can be calculated using the inserted length of the treatment instrument 4 from the treatment instrument insertion port 2F2. In another case where the medical device 1E includes an ultrasound probe as the treatment instrument 4, when the ultrasound probe is protruded from the treatment instrument port 2F, the protruded amount D can be calculated more accurately using the following method. That is, while the ultrasound probe is inserted through the channel 2F1 under the check of ultrasound images obtained by the ultrasound probe on the display, the number of bright pixels, in other words, the number of white pixels is suddenly increased in the ultrasound image when the ultrasound element portion of the ultrasound probe is protruded from the treatment instrument port 2F. That is, the ultrasound is reflected by the inner surface of the insertion section 2E while the ultrasound probe is located in the channel 2F1 because the inside of the insertion section 2E is coated with metal. However, after the ultrasound element portion of the ultrasound probe is protruded from the treatment instrument port 2F, the ultrasound is transmitted to the air layer in the tube cavity and the reflected ultrasound wave is decreased, which increases the number of white pixels in the ultrasound image, and the output from the ultrasound element is significantly changed. In this case, the length between the distal end portion and the ultrasound element portion of the ultrasound probe is known.

More specifically, first, a region of interest is set in an ultrasound image. Then, the number of pixels that have luminance with a predetermined threshold or more in the region of interest is counted, and when the number of pixels that have luminance with the predetermined threshold or more exceeds a predetermined number, the protrusion of the ultrasound probe from the channel 2F1 is detected. The region of interest may be a circle or square with the probe as a center, or the entire ultrasound image.

The above described method enables an accurate detection of the protrusion of the distal end of an ultrasound probe from the treatment instrument port 2F in the channel 2F1, thereby a protruded amount D can be more accurately calculated.

Third Embodiment

Figure 14:
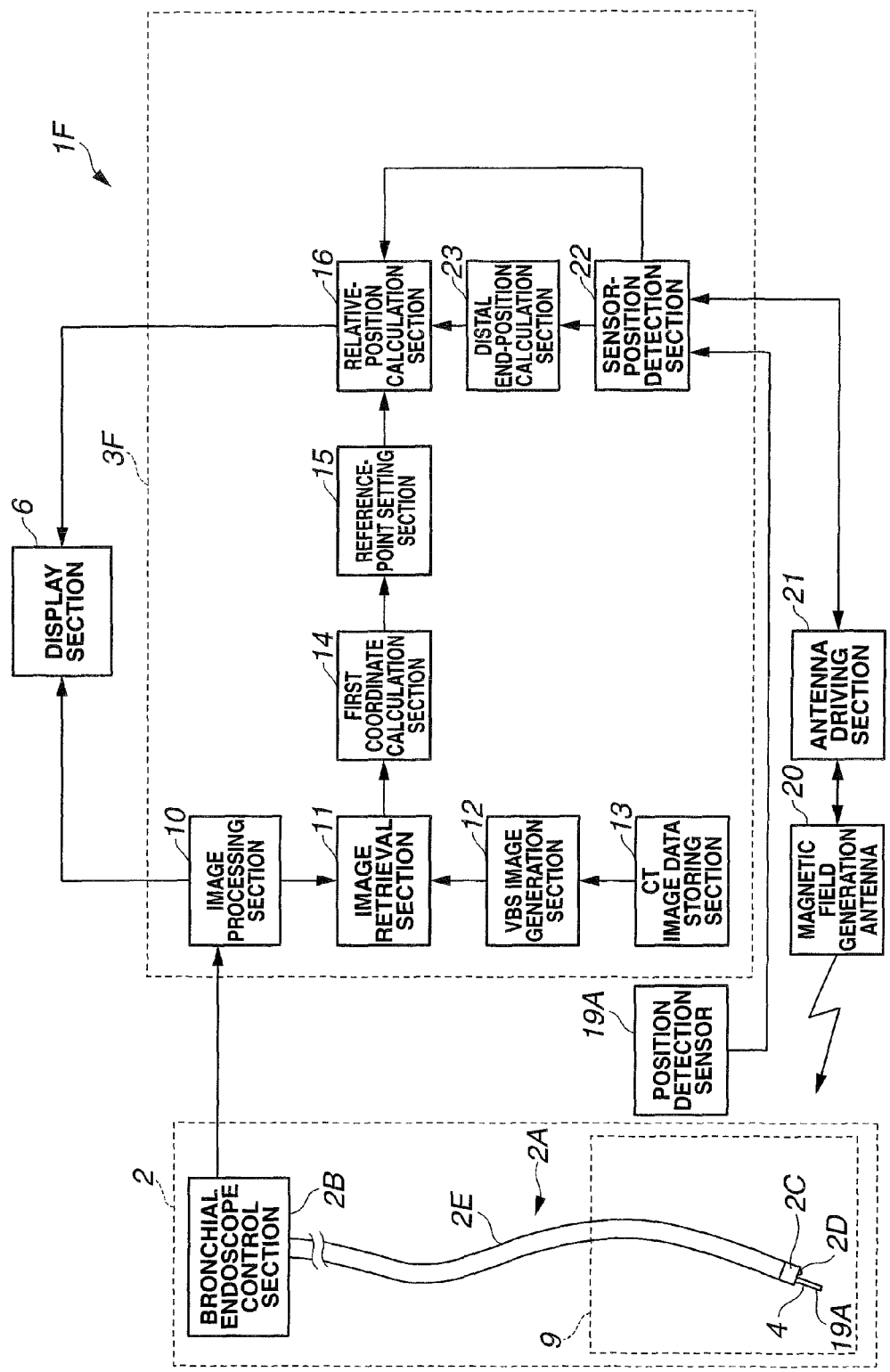
FIG. 14 is a configuration view showing a configuration of a medical device according to a third embodiment.

Now, with reference to the drawings, a medical device 1F of a third embodiment according to the present invention will be explained below. The medical device 1F is similar to the medical device 1 and the like, and the same components thereof are denoted by the same reference numerals, which will not be explained below. FIG. 14 is a configuration view showing a configuration of the medical device 1F of the present embodiment. In FIG. 14, the block for a position detection sensor 19A is positioned outside of the body for reason of representation, but the position detection sensor 19A is actually arranged at a predetermined position on the distal end portion of the treatment instrument 4.

As shown in FIG. 14, the medical device 1F includes: the position detection sensor 19A at a predetermined position on the treatment instrument 4; a sensor-position detection section 22 configured to detect the position of the position detection sensor 19A; and the relative-position calculation section 16 configured to calculate the relative position of the treatment instrument 4 to the reference point in a CT coordinate system based on the position of the treatment instrument 4 detected by the sensor-position detection section 22 and the reference point.

In the medical device 1F, the position detection sensor 19A is a magnetic field detection sensor, and detects the position of the treatment instrument 4 by detecting the magnetic field from a plurality of magnetic field generation antennas (not shown) placed outside of the patient 7. The magnetic field detection sensor may be MR sensor, hall element, or coil. The position detection sensor is not limited to a magnetic field detection sensor, but may be a position detection sensor such as optical strain sensor and strain gauge.

For example, the antenna driving section 21 causes a plurality of magnetic field generation antennas to generate alternating magnetic fields having different frequencies. The position detection sensor 19A distinguishes and detects each of the plurality of alternating magnetic fields having different frequencies, thereby the sensor-position detection section 22 can calculate the direction of each magnetic field generation antenna, which is used to detect the relative position of the position detection sensor 19A to the magnetic field generation antenna. Because the position of the position detection sensor 19A in the treatment instrument 4 is known, the distal end-position calculation section 23 is able to calculate the distal end position B1 of the treatment instrument 4.

Then, the relative-position calculation section calculates the relative position of the distal end position B1 of the treatment instrument 4 calculated by the distal end-position calculation section 23 to reference point A1.

The medical device 1F having the position detection sensor 19A provides an advantage, in addition to the effects provided by the medical device 1 and the like, that the relative position of the distal end position B1 of the treatment instrument 4 to reference point A1 is more accurately calculated.

Figure 15A:
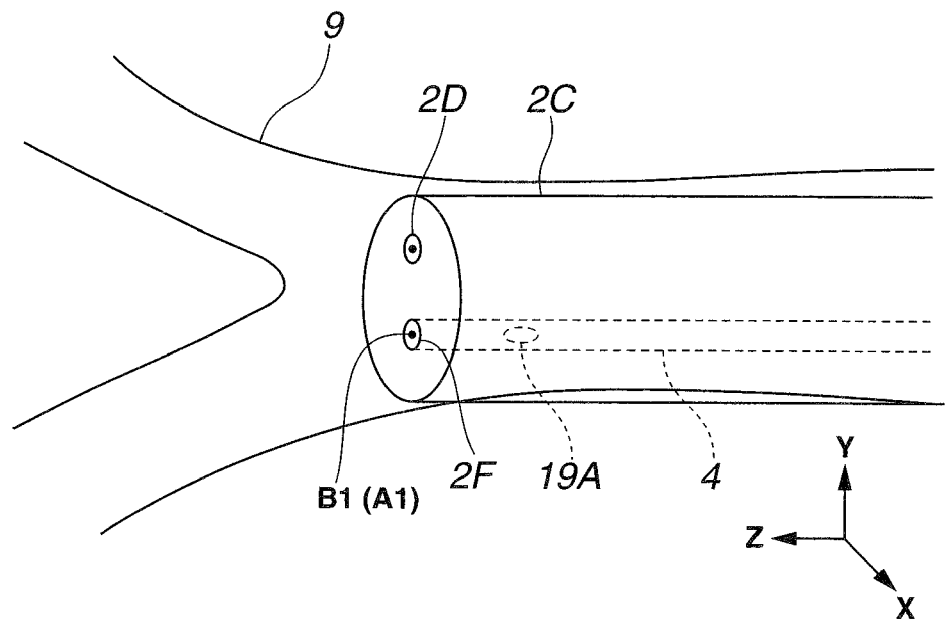
FIG. 15A is an illustrative view of a method for calculating a relative position of a distal end position of a treatment instrument using a medical device according to the third embodiment in a case where the distal end portion having a position detection sensor of the treatment instrument is in a treatment instrument port.
Figure 15B:
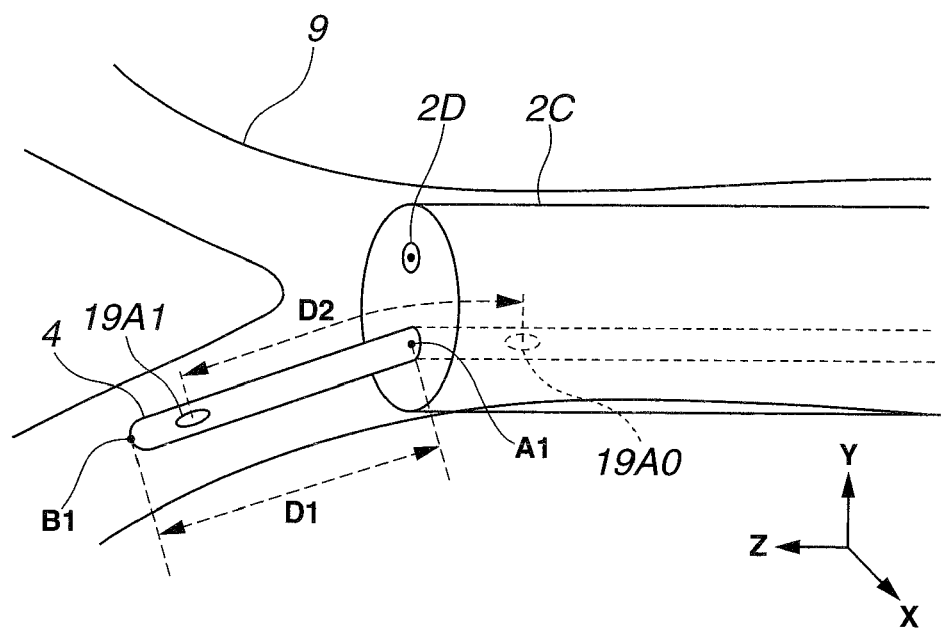
FIG. 15B is an illustrative view of a method for calculating a relative position of a distal end position of a treatment instrument using the medical device according to the third embodiment in a case where the distal end portion of the treatment instrument is protruded out of a treatment instrument port by a length.

FIGS. 15A and 15B are illustrative views explaining a method for calculating a relative position of the distal end position B1 of a treatment instrument 4 using a medical device 1F; FIG. 15A shows a case where the distal end B1 having the position detection sensor 19A of the treatment instrument 4 is in the treatment instrument port 2F; FIG. 15B shows a case where the distal end B1 of the treatment instrument 4 is protruded from the treatment instrument port 2F by a length D1.

The position detection sensor 19A moves as the state of the treatment instrument 4 shown in FIG. 15A is changed to the state shown in FIG. 15B. Then, the position 19A0 of the position detection sensor 19A before the movement shown in FIG. 15B and the position 19A1 of the position detection sensor 19A after the movement are detected by the sensor-position detection section 22. Based on the detection result, the distal end-position calculation section 23 calculates a moving distance D1. As explained above with FIGS. 13A and 13B, with the use of centerline information and the like, the relative-position calculation section 16 calculates the relative position of the distal end B1 of the treatment instrument 4 to the reference point A1 based on the moving distance D1.

As explained above, the medical device 1F provides an advantage, in addition to the effects provided by the medical device 1 and the like, that the position of the distal end position B1 can be transformed to a CT coordinate system even after the distal end position B1 moves, once the relative position between the reference point A1 in the CT coordinate system and the distal end position B1 of the treatment instrument in an endoscope coordinate system is calculated.

Fourth Embodiment

Figure 16:
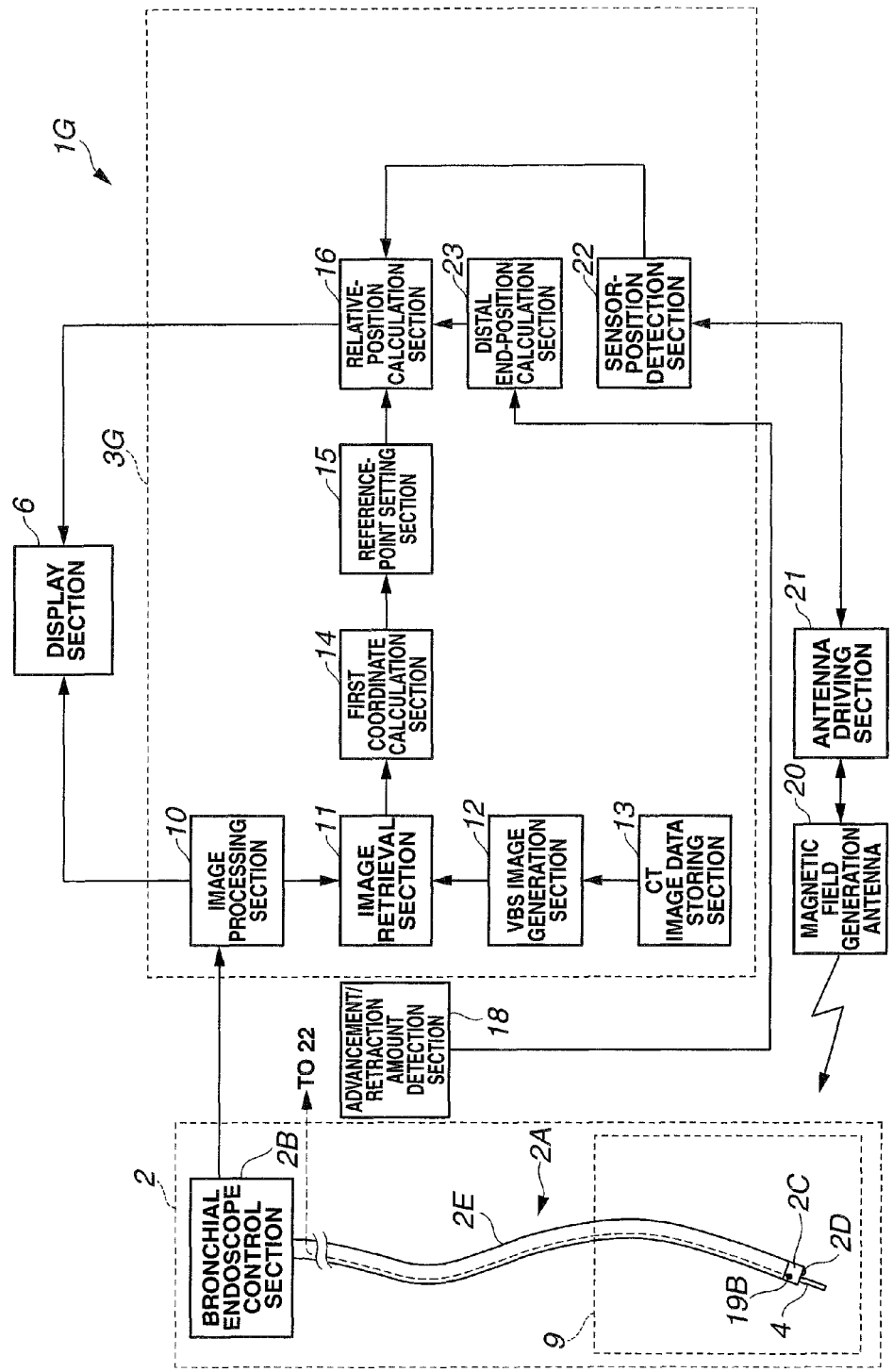
FIG. 16 is a configuration view showing a configuration of a medical device according to a fourth embodiment.

Now, with reference to the drawings, a medical device 1G of a fourth embodiment according to the present invention will be explained below. The medical device 1G is similar to the medical device 1 and the like, and the same components thereof are denoted by the same reference numerals, which will not be explained below. FIG. 16 is a configuration view showing a configuration of the medical device 1G of the embodiment according to the present invention.

As shown in FIG. 16, the medical device 1G includes the advancement/retraction amount detection section 18 configured to detect an amount of advancement/retraction of the treatment instrument 4, and the distal end-position calculation section 23 configured to calculate a distal end position based on the amount of advancement/retraction. The medical device 1G further includes the position detection sensor 19B at the distal end portion 2C of the endoscope, the magnetic field generation antenna 20, and the antenna driving section 21, so that the sensor-position detection section 22 can calculate the position of the position detection sensor 19B. Operations of the sensor-position detection section 22 are similar to those of the medical device 1F of the third embodiment.

Figure 17A:
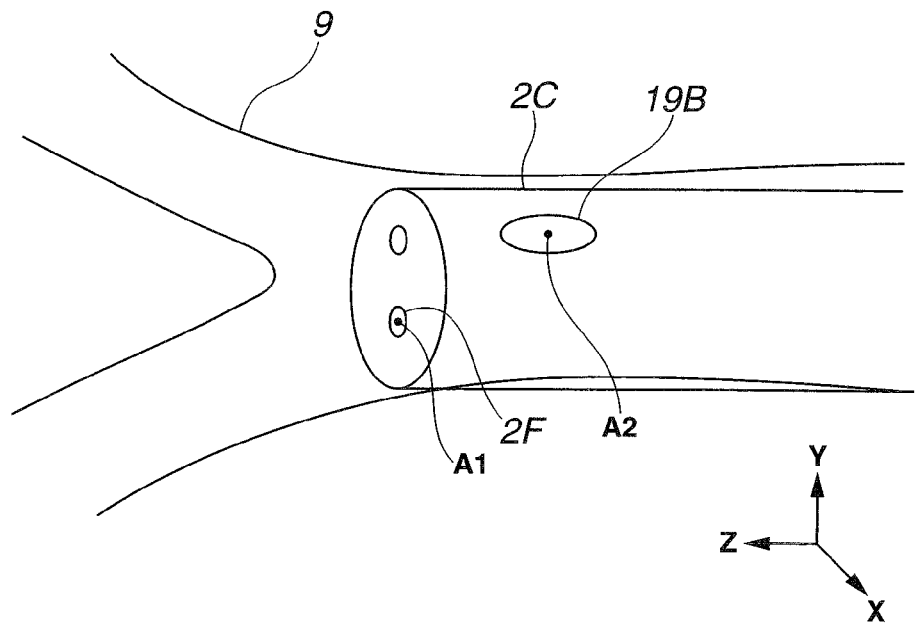
FIGS. 17A to 17C are illustrative schematic views of position detection and the like of a treatment instrument using the medical device of the fourth embodiment.
Figure 17B:
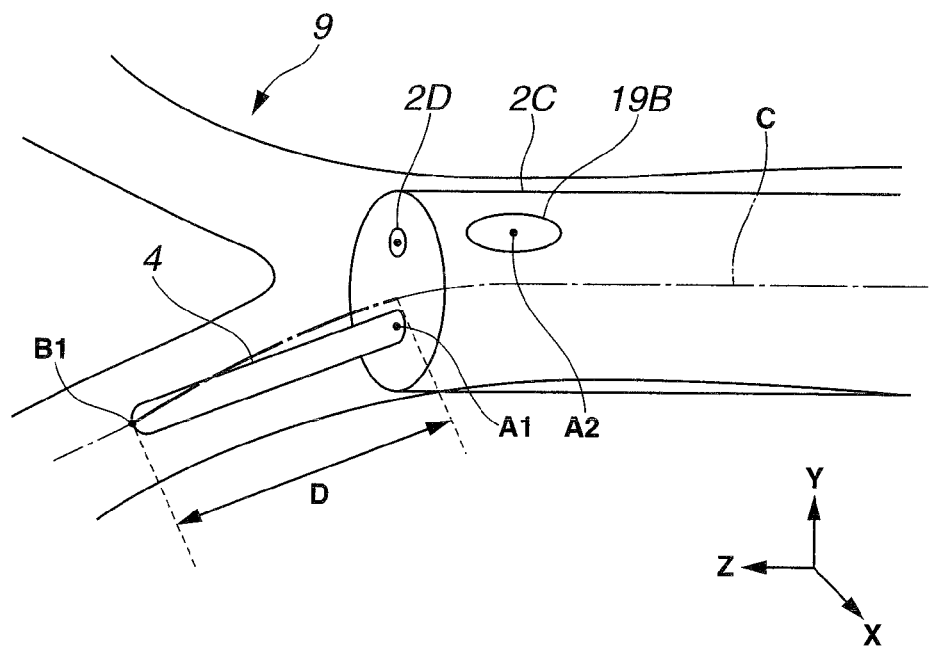
Figure 17C:
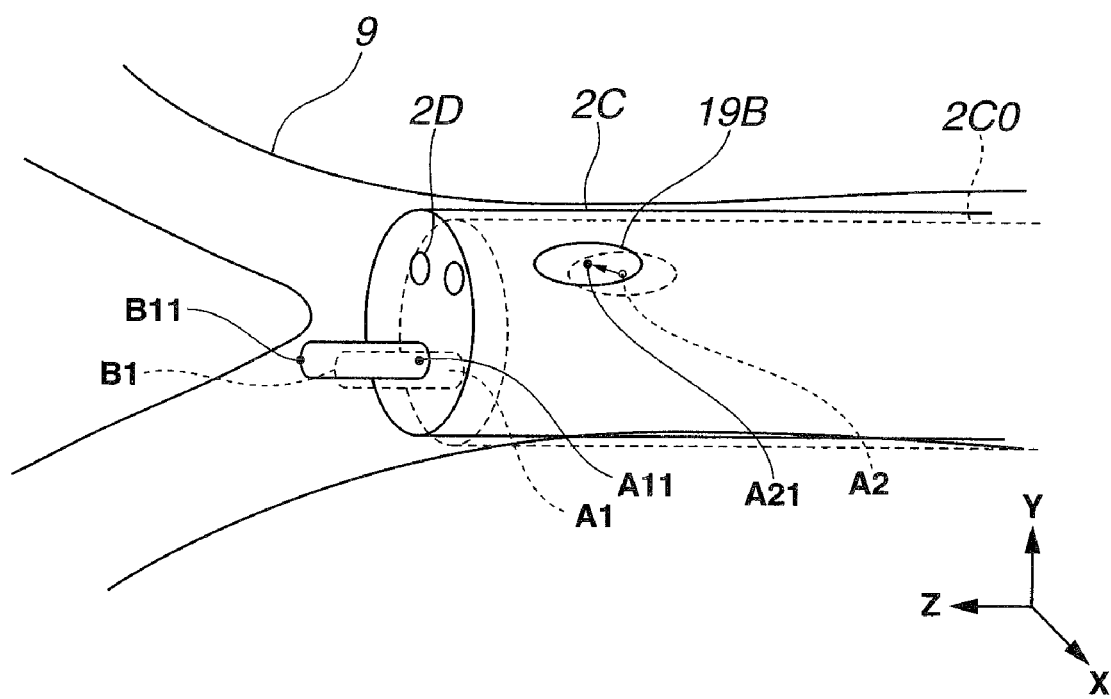

FIGS. 17A to 17C are illustrative schematic views of the position detection of the treatment instrument 4 in the medical device 1G of the present embodiment. Now, according to FIGS. 17A to 17C, the operations of a medical device 1G will be explained below.

First, as shown in FIG. 17A, the first coordinate calculation section 14 calculates a first coordinate point A0 using the line-of-sight parameters of a VBS image similar to a real image, and the reference-point setting section 15 sets a distal end point of the treatment instrument port 2F from which the distal end of the treatment instrument 4 is protruded, that is, the central position of the treatment instrument port 2F which is the distal opening of the endoscope as a reference point A1. At the same time, the sensor-position detection section 22 detects the position A2 of the position detection sensor 19B and transforms the detected position A2 to the already obtained reference point A1.

Furthermore, the advancement/retraction amount detection section 18 detects an amount of advancement/retraction D of the treatment instrument 4. Then, as shown in FIG. 17B, the relative-position calculation section 16 is able to calculate a treatment instrument distal end position B1 using the reference point A1 inputted from the sensor-position detection section 22 and the amount of advancement/retraction D inputted from the distal end-position calculation section 23. FIG. 17B shows the case where the protruding movement of the treatment instrument distal end position B1 is approximated to that along the centerline, but the protruding movement of the treatment instrument 4 may be approximated to be straight for calculation.

In addition, as shown in FIG. 17C, even when the distal end portion 2C moves from the position represented as a distal end portion 2C0, the reference point A1 can be calculated based on the value from the position detection sensor 19B after the position A2 of the position detection sensor 19B is associated with the reference point A1. In the medical device 1G, a reference point A11 is calculated using the position A21 of the position detection sensor 19B after the movement, so that the reference point A11 is used as a new reference point to calculate a treatment instrument distal end position B11 in a CT coordinate using an amount of advancement/retraction D.

Thus, the medical device 1G provides an advantage, in addition to the effects provided by the medical device 1 and the like, that the treatment instrument distal end position B1 is more accurately operated.

Fifth Embodiment

Figure 18:
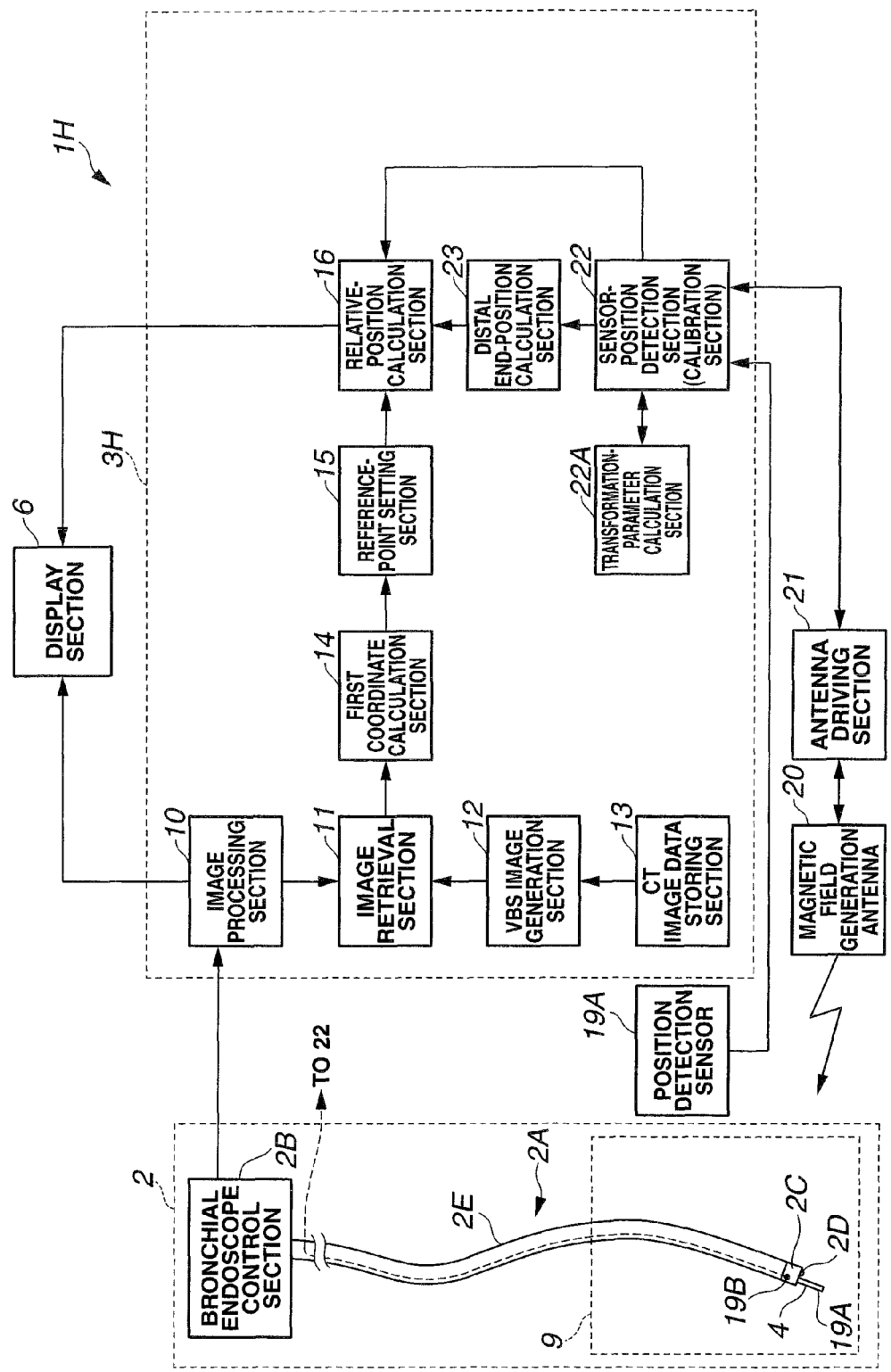
FIG. 18 is a configuration view showing a configuration of a medical device according to a fifth embodiment.

Now, with reference to the drawings, a medical device 1H of a fifth embodiment according to the present invention will be explained below. The medical device 1H is similar to the medical device 1 and the like, and the same components thereof are denoted by the same reference numerals, which will not be explained below. FIG. 18 is a configuration view showing a configuration of the medical device 1H of the embodiment according to the present invention. The position detection sensor 19A at the distal end portion of the treatment instrument 4 is shown as a block positioned outside of the body, and the position detection sensor 19B at the distal end portion 2C is simplified, for reason of representation. FIGS. 19A to 19D are illustrative schematic views of a position detection of the treatment instrument 4 in the medical device 1H of the present embodiment.

As shown in FIG. 19A to FIG. 19D, the medical device 1H includes a first position detection sensor 19A at a predetermined position near the distal end of the treatment instrument 4, and a second position detection sensor 19B at a predetermined position at the distal end portion 2C, and the sensor-position detection section 22 detects the positions of the first position detection sensor 19A and the second position detection sensor 19B. In a case where the physical positional relationship between the second position detection sensor 19B and the first position detection sensor is known, in the medical device 1H, the positional information detected by the first position detection sensor 19A can be transformed based on the positional information detected by the second position detection sensor 19B, and also the positional information detected by the second position detection sensor 19B can be transformed based on the positional information detected by the first position detection sensor 19A. That is, the medical device 1H includes a transformation-parameter calculation section 22A configured to calculate a transformation parameter to transform reference positions and reference directions of the first position detection sensor 19A and the second position detection sensor 19B to each other. The position of the first position detection sensor associated with the second position detection sensor reveals the position of the distal end of the treatment instrument.

That is, in the medical device 1H, the sensor-position detection section 22 also operates as a calibration section configured to transform positional information detected by the first position detection sensor 19A based on the positional information detected by the second position detection sensor 19B.

Now, with FIGS. 19A to 19D, the operations of a medical device 1H will be explained below.

Figure 19A:
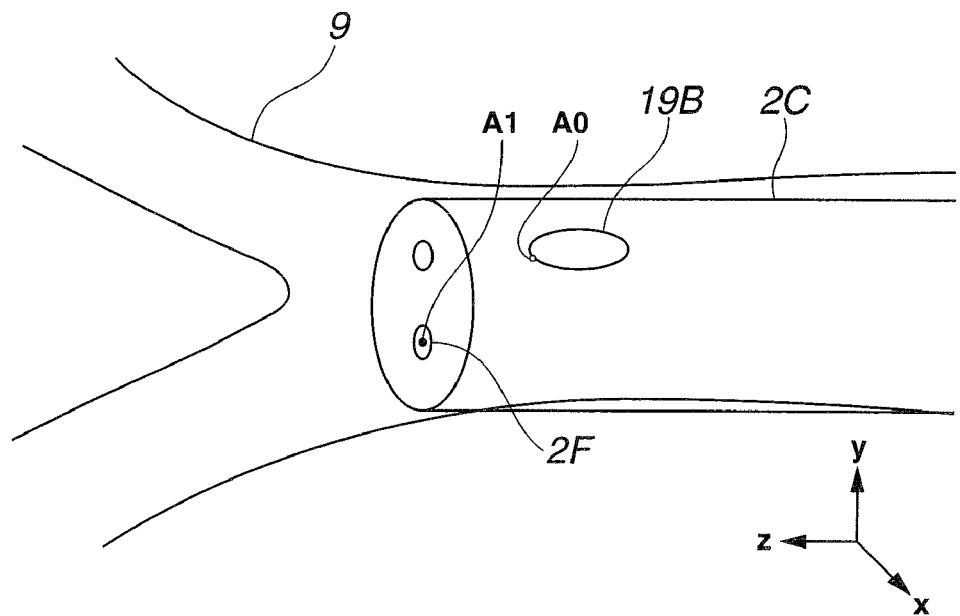
FIGS. 19A to 19D are illustrative schematic views of position detection and the like of a treatment instrument using the medical device of the fifth embodiment.

As shown in FIG. 19A, the first coordinate calculation section 14, first, calculates a first coordinate point A0 using the line-of-sight parameters of a VBS image similar to a real image, and the reference-point setting section 15 sets the distal end point of the treatment instrument port 2F from which the distal end of the treatment instrument 4 is protruded, that is, the central position of the treatment instrument port 2F which is the distal opening of the endoscope as a reference point A1.

Figure 19B:
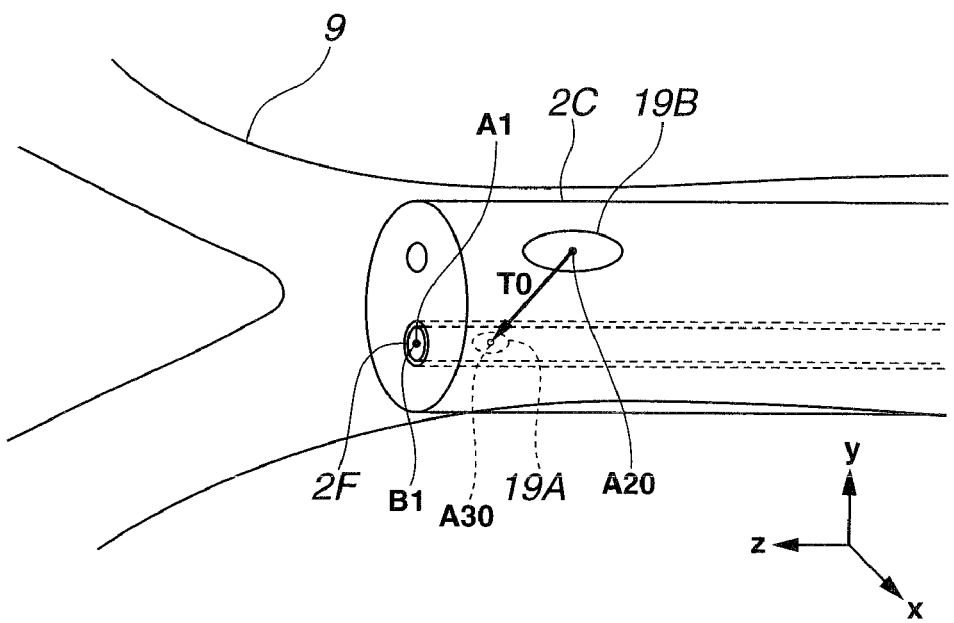

Next, as shown in FIG. 19B, when the position of the treatment instrument distal end B1 is aligned to the position of the treatment instrument port 2F, that is, the reference point A1, the sensor-position detection section 22 detects the position A30 of the first position detection sensor 19A and the position A20 of the second position detection sensor 19B.

Furthermore, the sensor-position detection section 22 operates as a calibration section to transform the position A30 of the first position detection sensor 19A based on position A20 of the second position detection sensor 19B. More specifically, the sensor-position detection section 22 calculates a transformation vector T0 according to the equation: "T0=A30−A20".

Figure 19C:
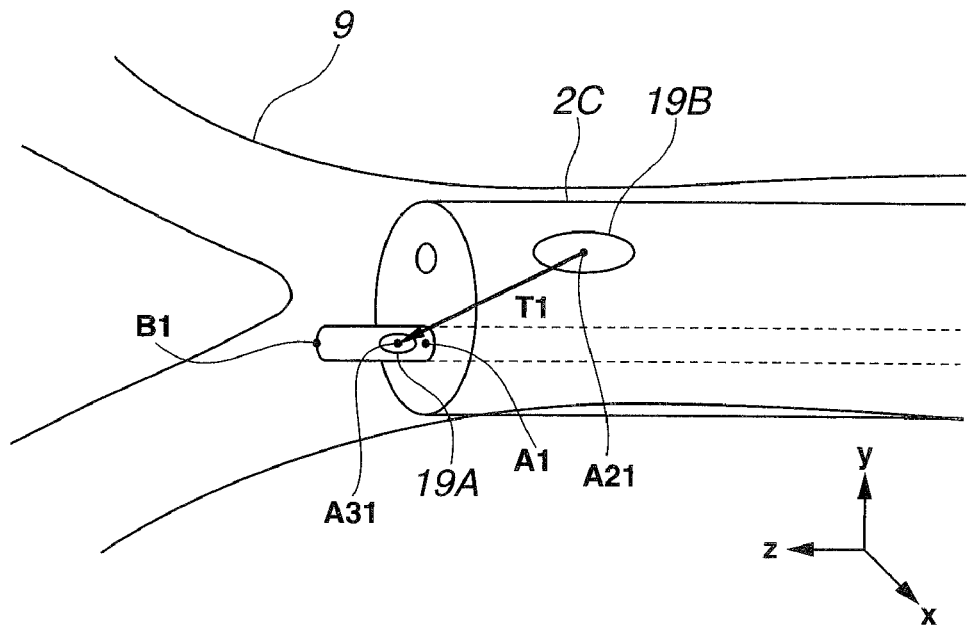

Next, when the treatment instrument 4 is protruded as shown in FIG. 19C, the position of the first position detection sensor 19A is moved to the position A31. Based on the position A21 of the second position detection sensor at this point of time, the transformation vector T1 can be calculated according to the equation: "T1=A31−A21". Then, the distal end-position calculation section 23 calculates the protrusion amount D according to the equation: "D=T1−T0".

Because the second position detection sensor 19B is arranged at the distal end portion 2C, the relationship between reference point A1 and the position A2 is not changed and can be easily calculated. That is, the reference point A1 and the position A2 are associated with each other, and the transformation vector T12 can be expressed as "T12=A1−A2". Thus, the relative-position calculation section 16 is able to calculate the position which is advanced from the reference point A1 by the protruded amount D on the centerline as the treatment instrument distal end position B1.

Figure 19D:
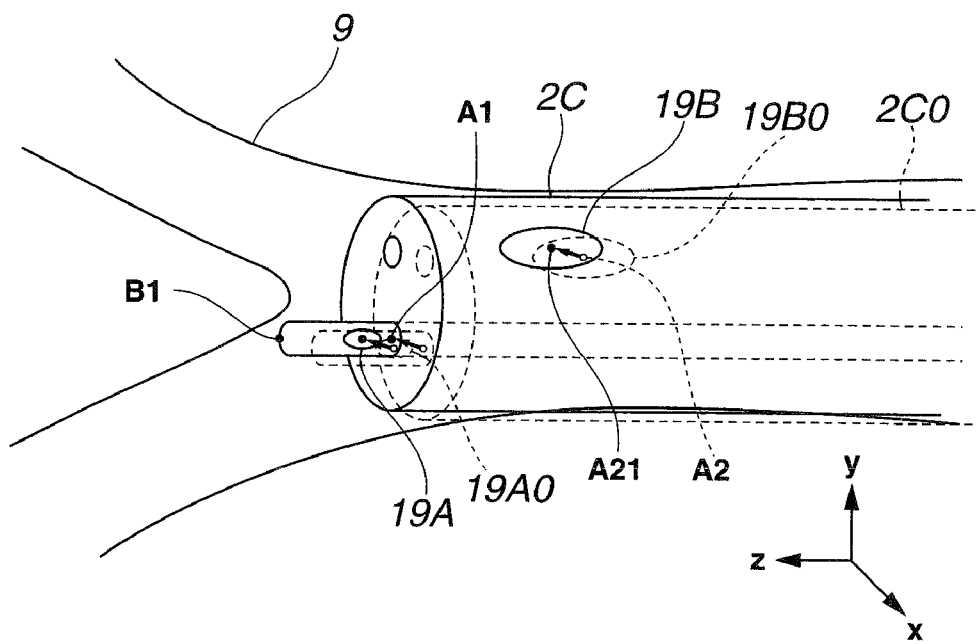

As shown in FIG. 19D, even when the distal end portion 2C moves from the position represented as the distal end portion 2C0, the distal end-position calculation section 23 is able to calculate the accurate position of the treatment instrument distal end B1 according to a CT coordinate system, by calculating a moving vector based on the position A2 of the second position detection sensor 19B before the movement and the position A21 after the movement, and calculating the reference point A1 based on the movement amount.

In the medical device 1H, preferably the sensor-position detection section 22 detects the positions of the first position detection sensor 19A and the second position detection sensor 19B when the medical instrument is protruded from the treatment instrument port 2F, and performs calibration for transforming the positional information detected by the first position detection sensor 19A to the positional information detected by the second position detection sensor 19B. The above operation is to decrease error information of the positions detected by the first position detection sensor 19A and the second position detection sensor 19B.

Therefore, the medical device 1H is able to provide more accurate operation of a treatment instrument by a surgeon to the target site 9G represented in a CT coordinate system than that of the medical device 1 and the like.

Figure 20:
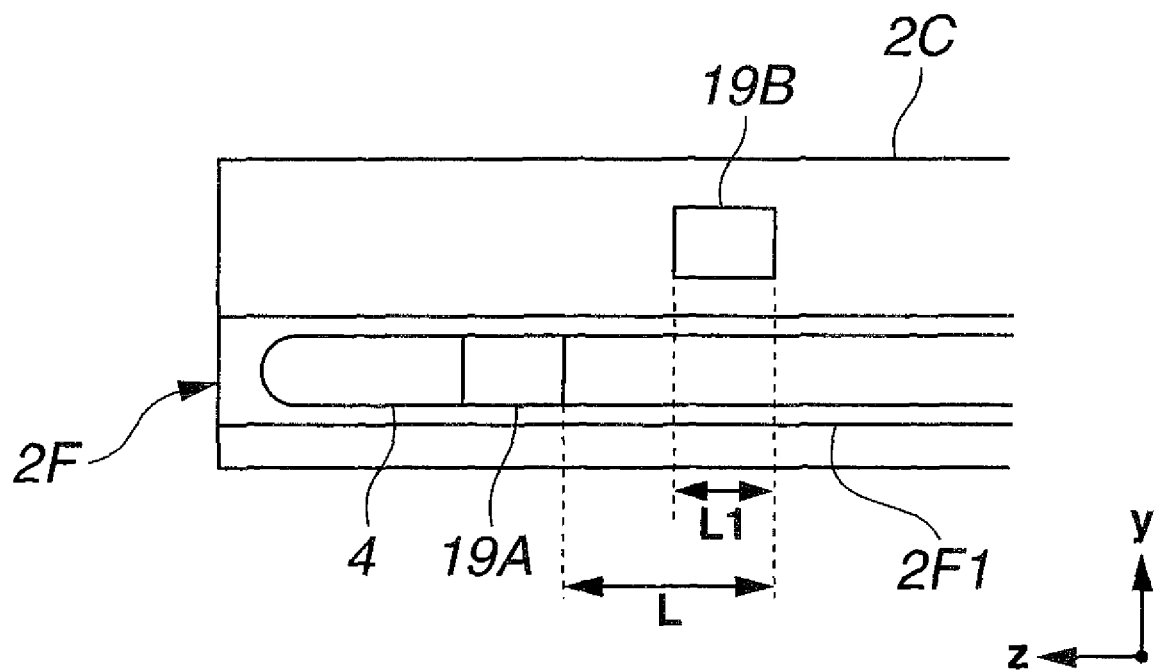
FIG. 20 is an illustrative schematic view of an arrangement of a sensor coil.

In the medical device 1H, when both of the first position detection sensor 19A and the second position detection sensor 19B are magnetic field sensing coils (hereinafter, referred to as "sensor coil" or "coil"), the relative positions in a position detection of the two magnetic field sensing coils should be cared. For example, as shown in FIG. 20, a position detection is preferably performed in a state where the relative positions of the two sensor coils, that is, the relative positions the first position detection sensor 19A and the second position detection sensor 19B are not overlapped with each other in the insertion direction that is the direction of Z-axis shown in FIG. 20.

At the overlapped positions, each of the magnetic field sensing coils disturbs the magnetic field, and the output from the sensor becomes unstable. The distance L between the first position detection sensor 19A and the second position detection sensor 19B that does not make the output from the sensor unstable, in other words, that does not influence the magnetic field depends on a configuration of the medical device, for example a coil shape and a generated magnetic field. Therefore, a distance L that does not make the output from the sensor unstable is measured in advance, so that a position detection can be performed with the first position detection sensor 19A and the second position detection sensor 19B being separated from each other by the distance L or more. For example, with the position detection sensor 19B having a length of L1, preferably the distance L is 0.5×L1 or more, and particularly preferably the distance L is equal to L1 or more.

The calculation of a first coordinate point, the setting of a reference point, and the calculation, calibration, and correction of a relative position in the above description are preferably performed in a stable state of the entire system. More specifically, for example, the stable state includes the case where the change amount of the position of the first position detection sensor 19A or second position detection sensor 19B, that is, the output is equal to or less than a predetermined position that was determined in advance. Alternatively, for example, the stable state includes the case where the change amount of the line-of-sight parameter is equal to or less than a predetermined position that was determined in advance. As already explained above, both of the sensor output and the line-of-sight parameter include six factors of positions (x, y, z) and angles ($\theta x$, $\theta y$, $\theta z$), and all of the six are preferably stable for the calibration and the like.

In the above description, the endoscope is the endoscope apparatus 2 having the elongated insertion section 2E, but a medical device of the present invention may be a capsule endoscope apparatus having an image pickup section 2D that is able to pickup an image of tube cavity in the body of a patient 7, which also provides the same operational effects as those of the endoscope apparatus 2 having the elongated insertion section 2E.

A medical device of an embodiment according to the present invention includes: a treatment instrument or probe having a first position detection sensor for examination or treatment in bronchus of a subject based on a reference point; a sensor-position detection section configured to detect a position of the first position detection sensor; an insertion section that is insertable through the bronchus and has a channel formed therein through which the treatment instrument or the probe is insertable, and has an opening of the channel and an image pickup section that is able to pickup an image of the bronchus at a distal end portion thereof; a virtual endoscopic image generation section configured to generate a plurality of virtual endoscopic images in the bronchus from a plurality of line-of-sight positions based on three-dimensional image data of the subject that is obtained in advance, and to generate a more highly similar virtual endoscopic image based on the information of the most highly similar virtual endoscopic image that is retrieved by an image retrieval section configured to retrieve the virtual endoscopic image most highly similar to the endoscopic image of the bronchus picked up by the image pickup section among the plurality of already generated virtual endoscopic images; a reference-point setting section configured to set the position of the opening as the reference point based on the line-of-sight position of the more highly similar virtual endoscopic image; a sensor-position detection section configured to detect a position of the treatment instrument or the probe relative to the reference point; and a relative-position calculation section configured to calculate a relative position of the treatment instrument or the probe to the reference point based on the position of the treatment instrument or the probe detected by the sensor-position detection section and the reference point.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A medical device, comprising:
    an image pickup section that is able to pick up an image of a tube cavity in a subject, the image pickup section disposed at a distal end portion of an endoscope;
    a medical instrument for examination or treatment in the tube cavity based on a reference point, the medical instrument configured to protrude from the distal end portion;
    a virtual endoscopic image generation section configured to generate a virtual endoscopic image in the tube cavity from a plurality of different line-of-sight positions using three-dimensional image data of the subject that is obtained in advance;
    an image retrieval section configured to retrieve the virtual endoscopic image highly similar to the endoscopic image of the tube cavity picked up by the image pickup section;
    a reference-point setting section configured to set a predetermined position near the image pickup section at the distal end portion as the reference point based on the line-of-sight position of the highly similar virtual endoscopic image; and
    a relative-position calculation section for calculating a relative position of the medical instrument protruded from the distal end portion to the reference point.

2. The medical device according to claim 1, wherein
    the virtual endoscopic image generating section generates a more highly similar virtual endoscopic image based on the information from the image retrieval section, and
    the reference-point setting section sets the reference point at the distal end portion based on the line-of-sight position of the more highly similar virtual endoscopic image.

3. The medical device according to claim 1, wherein
    the image retrieval section retrieves the most highly similar virtual endoscopic image among the plurality of the virtual endoscopic images generated by the virtual endoscopic image generation section in advance,
    the virtual endoscopic image generation section generates a more highly similar virtual endoscopic image based on the information of the most highly similar virtual endoscopic image retrieved by the image retrieval section, and
    the reference-point setting section sets the reference point at the distal end portion based on the line-of-sight position of the more highly similar virtual endoscopic image.

4. The medical device according to claim 1, further comprising:
    an image-position calculation section configured to detect the position of the medical instrument from the endoscopic image picked up by the image pickup section, and wherein
    the relative-position calculation section calculates the relative position based on the position of the medical instrument detected by the image-position calculation section and the reference point at the distal end portion.

5. The medical device according to claim 1, further comprising:
    an insertion section that is insertable through the tube cavity, has a channel formed therein through which the medical instrument is insertable, and has an opening of the channel and the image pickup section at a distal end portion thereof, and wherein
    the reference point is positioned at the opening.

6. The medical device according to claim 1, wherein
    the medical instrument is a treatment instrument or a probe.

* * * * *